US012458781B2

(12) United States Patent
Albus et al.

(10) Patent No.: US 12,458,781 B2
(45) Date of Patent: Nov. 4, 2025

(54) INTRAVENOUS CATHETER LOCK

(71) Applicant: Mayo Foundation for Medical Education and Research, Rochester, MN (US)

(72) Inventors: Michael Albus, Jacksonville, FL (US); Kara J. Bragg, Saint Johns, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 19/045,847

(22) Filed: Feb. 5, 2025

(65) Prior Publication Data

US 2025/0195845 A1 Jun. 19, 2025

Related U.S. Application Data

(63) Continuation of application No. 17/480,726, filed on Sep. 21, 2021, now Pat. No. 12,329,919.

(60) Provisional application No. 63/086,324, filed on Oct. 1, 2020.

(51) Int. Cl.
*A61M 25/06* (2006.01)

(52) U.S. Cl.
CPC .... *A61M 25/0625* (2013.01); *A61M 25/0606* (2013.01)

(58) Field of Classification Search
CPC ............ A61M 25/02; A61M 2025/024; A61M 2025/0675; A61M 39/1011; A61M 2039/1016; E05B 17/04; E05B 17/044; E05B 17/047; E05B 29/00
See application file for complete search history.

(56) References Cited

U.S. PATENT DOCUMENTS

| | | | | |
|---|---|---|---|---|
| 7,484,769 | B2 * | 2/2009 | Domash | A61M 39/12 285/401 |
| 8,603,022 | B2 * | 12/2013 | Lyons | A61M 39/162 604/6.16 |
| 9,440,061 | B2 * | 9/2016 | Yanik | A61M 39/1011 |
| 10,518,076 | B2 * | 12/2019 | Christie | A61M 39/1011 |
| 2002/0000027 | A1 | 1/2002 | Andersen et al. | |
| 2022/0105317 | A1 | 4/2022 | Albus et al. | |

* cited by examiner

*Primary Examiner* — Laura A Bouchelle
(74) *Attorney, Agent, or Firm* — Fish & Richardson P.C.

(57) ABSTRACT

A catheter lock system includes a clamshell housing comprising a body and a cover; one or more interlocking tabs of the body having a hook feature; compatible interlocking tabs of the cover configured to releasably engage with the interlocking tabs of the body; a key with one or more protrusions arranged at two different angles; one or more lock disc cams including a cam feature; wherein a rotation of the key is operable to cause the interlocking tabs of the body to release from the compatible interlocking tabs of the cover using each of the one or more protrusions of the key.

17 Claims, 22 Drawing Sheets

INTRAVENOUS CATHETER LOCK

CROSS-REFERENCE TO RELATED APPLICATIONS

This application is a continuation of U.S. patent application Ser. No. 17/480,726 filed on Sep. 21, 2021, which claims the benefit of U.S. Patent Application Ser. No. 63/086,324 filed on Oct. 1, 2020. The disclosure of the prior applications are considered part of (and are incorporated by reference in) the disclosure of this application.

BACKGROUND

1. Technical Field

This document relates to devices and methods for providing an intravenous (IV) catheter lock system. For example, the catheter lock system prevents patient access to an IV catheter.

2. Background Information

The human population has a long-standing opioid and substance abuse crisis. This problem is exacerbated in times of a pandemic, such as the Coronavirus (COVID-19) pandemic, which introduce significant additional social stressors.

Opioid and substance abuse addicts will often seek hospital care knowing that hospital staff will provide IV access. Unfortunately, these patients also use this IV access to inject drugs while under hospital care. These drugs include illegal substances such as Heroin, Cocaine, Methamphetamine, Ecstasy Ketamine, PCP, and legal prescription drugs like Vicodin and Adderall that are abused by the patient.

Sometimes these patients are left alone in hospital rooms (e.g., in scenarios where direct observation of the patient's IV is not always possible), giving the patient the opportunity to inject drugs into the IV when no one is looking. Worst still, sometimes these patients are sent home with the IV access in place, giving the patient the freedom to inject drugs into the IV at home. This misuse of IVs is a frequent source of prolonged hospitalizations, infections and can be fatal if the patient overdoses. Not to mention this causes a burden on the health care system in general.

A catheter is a thin tube made from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications.

SUMMARY

This document describes devices and methods for locking an IV catheter using a catheter lock system. The catheter lock system prevents an IV catheter from being abused by patients. In some situations, a patient will use or abuse the IV catheter to inject drugs into their body. By requiring a key for access to a catheter lock system, access to the IV catheter is restricted to people with a need for access (e.g., doctors, nurses, etc.).

The catheter lock system controls access to intravenous lines at multiple sites including but not limited to the hub and Y-ports of both central and peripheral catheters. The catheter lock system can be set to an institution specific key limiting access by individuals who may have obtained a key from a different facility.

The catheter lock system is usable by all patients receiving pain medication or otherwise deemed high risk by a scoring tool. It enables therapy for all patients where previously some patients may have been denied IV access due to high risk of abuse. The catheter lock system is easy to access and MRI compatible.

The catheter lock system offers hospital staff peace of mind knowing that patients are protected. The catheter lock system significantly reduces the cognitive load required by hospital staff allowing them to more efficiently care for all patients.

In some implementations, the catheter lock system is used as part of an IV kit and attached at the time of IV placement. The catheter lock system locks with an institution specific key and protect the hub as well as all tubing access points. The catheter lock system is easily removed by staff for routine or emergent IV access via the key but inaccessible to the patient, who would not have access to the key.

The catheter lock systems described herein can be used in in-hospital and outpatient settings such as the emergency department, in-patient wards, and post-anesthesia care units (PACU). The catheter lock systems described herein can be used at home or in a vehicle. In this way, the catheter lock systems described herein are applicable to catheter ports in a variety of scenarios.

A catheter lock system includes a clamshell housing comprising a body and a cover pivotably connected via a hinged axis; one or more interlocking tabs of the body protruding perpendicularly from an inside surface of the body, each interlocking tab of the one or more interlocking tabs having a hook feature; compatible interlocking tabs of the cover configured to releasably engage with the interlocking tabs of the body; a key with one or more protrusions arranged along a shaft of the key, the one or more protrusions being arranged at two different angles along a circumference of the shaft of the key, the two different angles being 90 degrees apart, each protrusion of the one or more protrusions having a flat surface; one or more lock disc cams comprising one or more openings, each opening of the one or more openings arranged 90 degrees relative to each other, each lock disc cam of the one or more lock disc cams comprising a cam feature; wherein a rotation of the key is operable to cause the interlocking tabs of the body to release from the compatible interlocking tabs of the cover using each of the one or more protrusions of the key.

In some implementations, each interlocking tab of the body is arranged along an axis parallel to the hinged axis with a space between the one or more interlocking tabs. In some cases, the catheter lock system further comprises one or more lock disc flanges arranged in the space between the one or more lock disc cams.

In some implementations, each lock disc cam comprises at least two recesses arranged at different angles along an outer circumference of the each lock disc.

In some implementations, each lock disc cam is rotatable before encoding the catheter lock system with the key and not rotatable after encoding the catheter lock system with the key.

In some implementations, the catheter lock system is configured to be encoded with the key upon an initial rotation of the key within the catheter lock system.

In some implementations, the flat surface of each protrusion of the key arranged at a first angle is configured engage the respective cam features of the respective lock disc cams.

In some cases, the flat surface of each protrusion of the key arranged at a second angle is configured engage a respective sidewall of the respective one or more interlocking tabs of the body.

In some implementations, each opening of the one or more lock disc cams is configured to slidably receive one of the one or more protrusions of the key.

In some implementations, the cam feature of each lock disc cam protrudes along a centerline of the lock disc cam.

In some implementations, the catheter lock system comprises one or more lock disc flanges operable to prevent rotation of the key when at least one protrusion of the one or more protrusions of the key engage with a flat surface of at least one of the one or more lock disc flanges.

In some implementations, the body comprises shield feature protruding from the inside surface configured to protect the key from damaging a catheter.

In some implementations, the clamshell housing comprises at least two access ports for enabling a port of a catheter to be received within the clamshell housing and enabling the catheter to be connected to a drug delivery system such that a drug of the drug delivery system is deliverable to a patient via the catheter when the clamshell housing is closed and locked.

Some catheter lock systems include a base housing comprising a top surface defining a plurality of recesses, each recess comprising a sidewall and a bottom surface, each bottom surface comprising a cylindrical recess containing a spring-loaded pin configured to slide along an axis of the cylindrical recess. Some catheter lock systems include an upper housing comprising a plurality of protrusions configured to be received by the plurality of recesses, each protrusion configured to engage one of the spring-loaded pins, wherein the upper housing is configured to slide along a direction perpendicular to the axis of the cylindrical recess when the protrusions are received by the plurality of recesses. In some examples, each protrusion comprises a cylindrical hole extending through the protrusion, the cylindrical hole containing a settable pin being settable between a first length and a second length longer than the first length, each settable pin configured to engage one of the spring-loaded pins to cause the spring-loaded pin to slide into the cylindrical recess. Some catheter lock systems include a key comprising a plurality of protrusions, each protrusion configured to contact one of the settable pins and cause the catheter lock system to move from a locked configuration to an unlocked configuration.

In some implementations, the plurality of protrusions comprise a hook-shaped portion configured to engage a counterpart hook-shaped recess of the base housing. In some implementations, the base housing comprises a central region for housing a catheter port and a catheter cap.

In some implementations, the base housing comprises at least two catheter ports arranged in a "Y" configuration.

In some implementations, at least one of the at least two catheter ports projects from a bottom surface of the base housing.

In some implementations, catheter lock systems also include a cover configured to be inserted over the upper housing, the cover comprising a plurality of holes, wherein each protrusion of the key is configured to slide through one of the holes.

In some implementations, the key comprises a flat plate portion and each of the protrusions of the key project from the same side of the flat plate portion.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1A is an isometric view of the protective clamshell in a closed configuration. FIG. 1B is a top view of the protective clamshell in an open configuration. FIG. 1C is an exploded assembly view of the protective clamshell in the open configuration.

FIG. 6A is an isometric view of the protective clamshell in a closed configuration. FIG. 6B is a top view of the protective clamshell in an open configuration. FIG. 6C is an exploded assembly view of the protective clamshell in the open configuration. FIG. 6D is a housing of the protective clamshell. FIG. 6E is a partially assembled view of the protective clamshell in the open configuration. FIG. 6F is a rendering of the protective clamshell in the closed configuration.

FIG. 7A is an isometric view of the protective clamshell in an open configuration. FIG. 7B is a perspective cross-section view of the protective clamshell in an open configuration.

FIG. 8A shows the wafer without a tab and FIG. 8B shows the water with the tab.

FIG. 12A is a perspective view of the catheter lock system in a closed configuration. FIG. 12B is a perspective view of the catheter lock system in an open configuration. FIG. 12C is a perspective view of a base housing, an upper housing, and a lid of the catheter lock system in the open configuration. FIG. 12D is a perspective view of the underside of the catheter lock system in the closed configuration.

Like reference numbers represent corresponding parts throughout.

DETAILED DESCRIPTION

This document describes devices and methods for locking an IV catheter. A catheter lock system prevents an IV catheter from being abused by patients. In some situations, a patient will use or abuse the IV catheter to inject drugs into their body. By requiring a key for access to a catheter lock system, access to the IV catheter is restricted to people with a need for access (e.g., doctors, nurses, etc.).

While described in reference to IV catheters, the catheter lock systems described in this specification are not limited to any particular IV line. For example, peripheral as well as central lines are compatible with the catheter lock systems described in this specification.

Figure 1B:
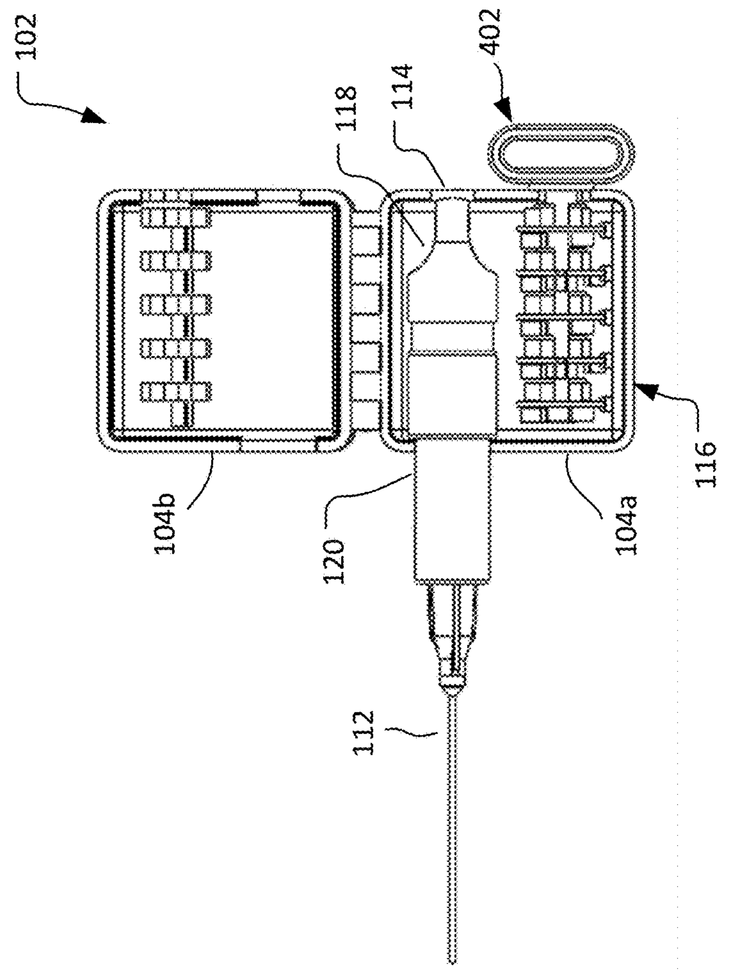
FIGS. 1A-1C are views of a protective clamshell with one port.
Figure 1A:
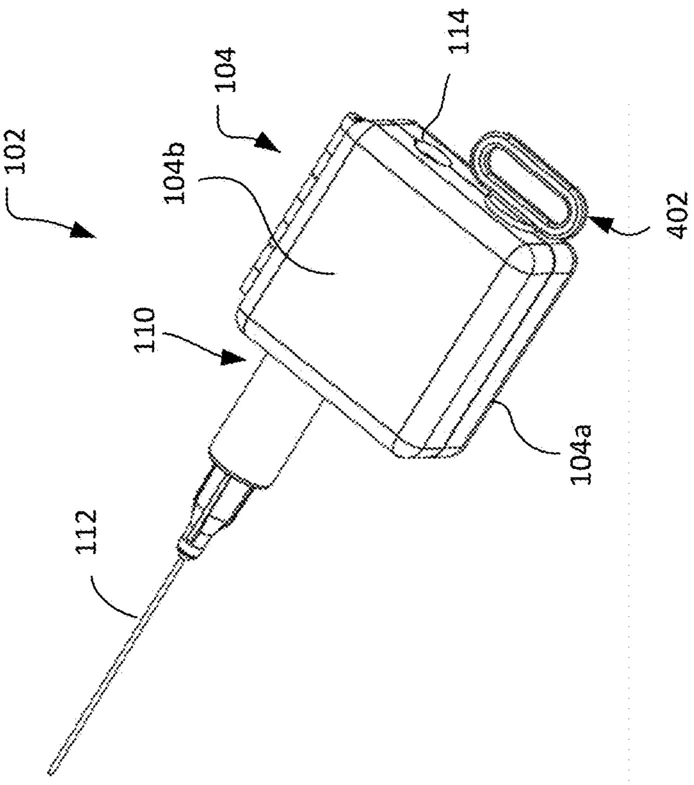

FIG. 1A is an isometric view of a catheter lock system 102 in a closed configuration. The catheter lock system 102 includes a clamshell housing 104. The clamshell housing 104 includes a lower housing or body 104*a* and an upper housing or cover 104*b* hinged (i.e., pivotably connected) together along an axis 106 so that clamshell housing 104 can be pivoted between an open and closed configuration.

The clamshell housing 104 includes an access port for a key 402. The key is used to unlock a locking mechanism to unlock the catheter lock system 102. The details of the locking mechanism will be described in further detail below.

The clamshell housing 104 includes an access port 110 for an IV catheter 112. A diameter of the access port 110 is smaller than a diameter of a housing 120 of the IV catheter 112 such that the IV catheter 112 cannot be pulled out of the catheter lock system 102 when closed and locked.

The clamshell housing 104 includes an access port 114 for a supply line (not shown) for the IV catheter 112. The supply line supplies a drug to the IV catheter 112 so that the drug flows into the patient even when the catheter lock system 102 is closed and locked. In other words, the clamshell housing 104 includes at least two access ports 110, 114 for enabling a port of the IV catheter 112 to be received within the clamshell housing 104 and enabling the IV catheter 112 to be connected to a drug delivery system (not shown) such that a drug of the drug delivery system is deliverable to a patient via the IV catheter 112 when the clamshell housing 104 is closed and locked.

FIG. 1B is a top view of the catheter lock system 102 in an open configuration. The catheter lock system 102 includes a locking mechanism 116 that is used in combination with the key 402 to lock and unlock the catheter lock system 102. A cap 118 of the IV catheter 112 is used to seal the IV catheter 112. The cap is removable from the housing 120 of the IV catheter 112 via a friction fit connection when the catheter lock system 102 is in the open configuration and not removable from the housing 120 when the catheter lock system 102 is in the closed configuration (as shown in FIG. 1A). Once removed, a medical professional can insert a supply line through the access port 114 of the clamshell housing 104 and connect it with a port 124 (shown in FIG. 1C) of the IV catheter port so that a drug of the supply line can travel to the patient.

Figure 1C:
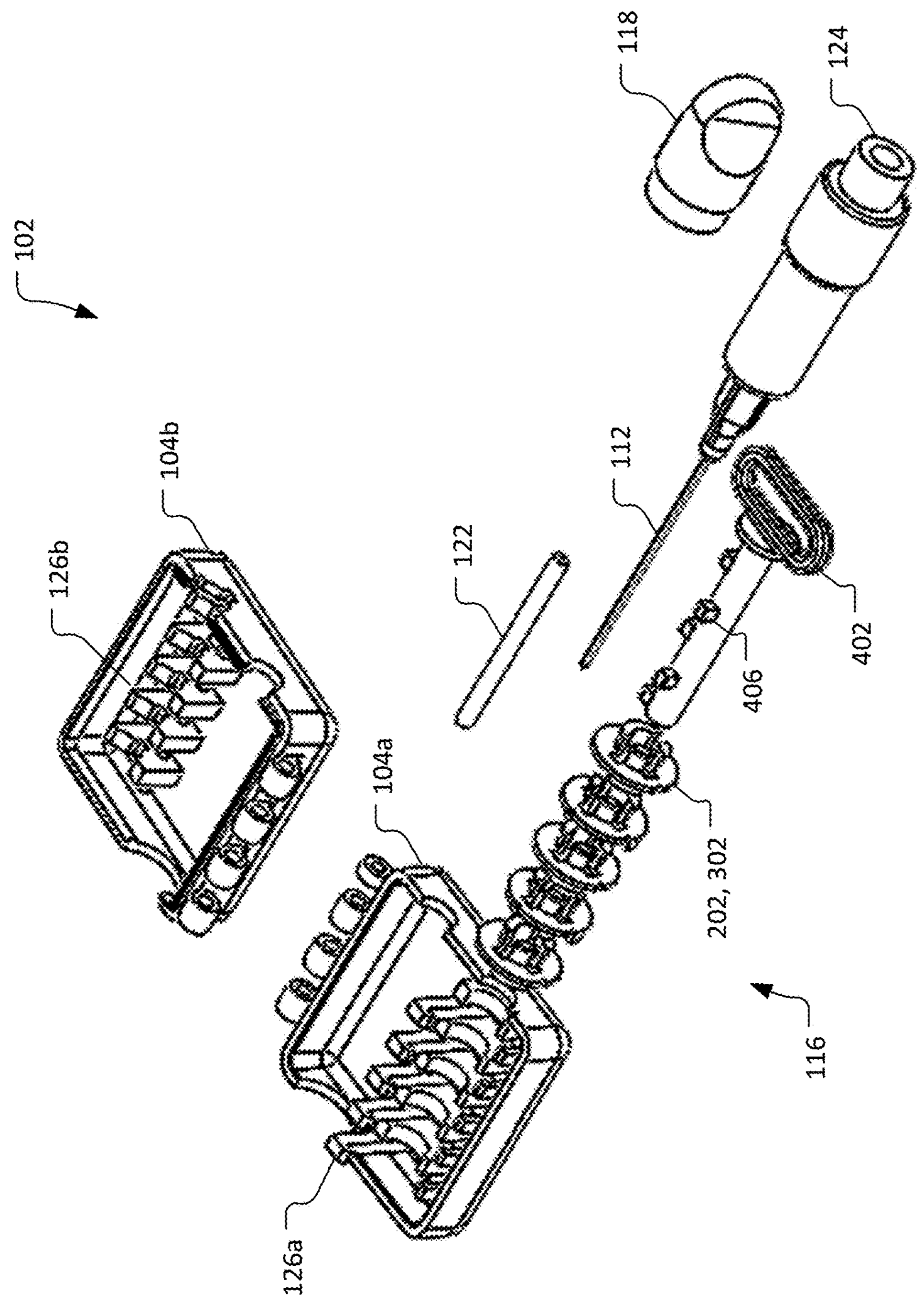

FIG. 1C is an exploded assembly view of the catheter lock system 102 in the open configuration. A pin 122 hinges the body 104*a* to the cover 104*b*. The body 104*a* includes a series of one or more interlocking tabs 126*a* that protrude perpendicularly from an inside surface of the body 104*a* that engage to a counterpart series of interlocking tabs 126*b* protruding from an inside surface of the cover 104*b*. Each interlocking tab 126*b* of the body 104*a* is arranged along an axis parallel to the hinged axis 106 with a space between the one or more interlocking tabs 126*b*. Each interlocking tab 126*b* includes a hook feature (see, e.g., the hook feature 620 shown in FIG. 6E) on an end away from the inside surface of the body 104*a*.

When the cover 104*b* is closed against the body 104*a*, the interlocking tabs 126*a*, 126*b* engage each other so the cover 104*b* cannot be opened without the key 402 being inserted and rotated within the catheter lock system 102. In the implementation shown, five interlocking tabs 126*b* are used. In some implementations, less than five or more than five interlocking tabs 126*b* are used. The key 402 includes a pattern of protrusions 406 arranged on a top surface of the key and on a side surface of the key 402. In the implementation shown, two protrusions 406 are on the top surface of the key 402 and three protrusions 406 are on the side of the key 402. When the key 402 is inserted into the catheter lock system 102, the protrusions 406 pass through a series of lock disc flanges 202 and engage with either the interlocking tabs 126*a* of the body 104*a* directly or engage with cam features of a series of lock disc cams 302.

Figure 2:
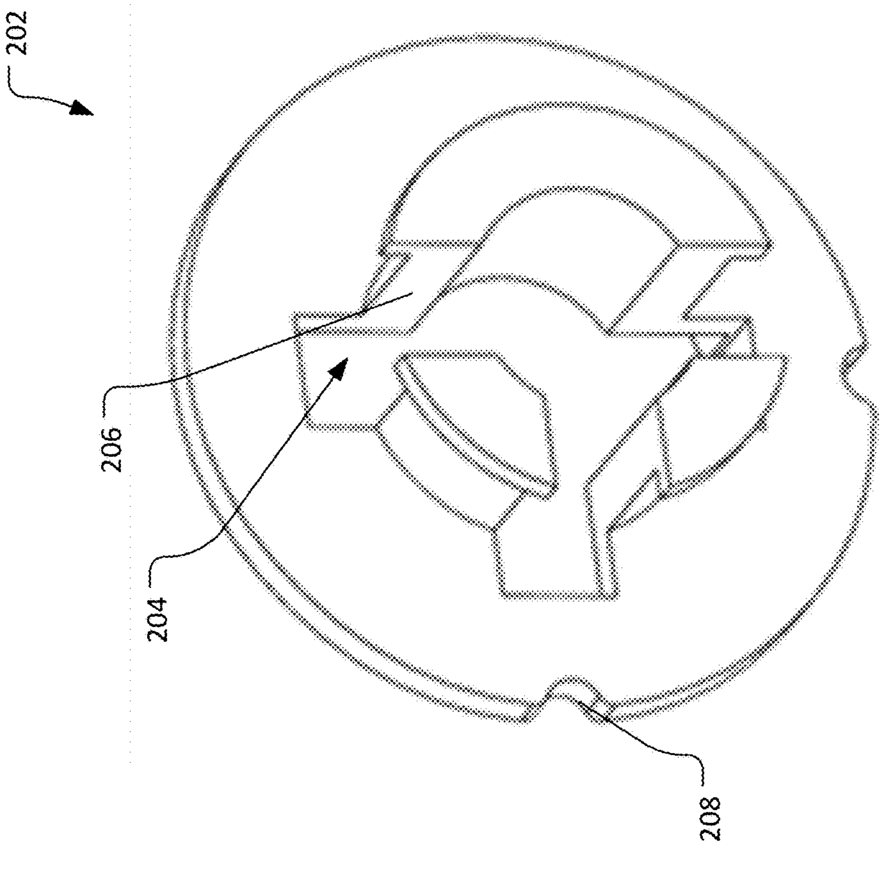
FIG. 2 is a perspective view of a lock disc flange for a locking mechanism.

FIG. 2 is a perspective view of a lock disc flange 202 for the locking mechanism 116. One or more lock disc flanges 202 act as a spacer along the axis of the key 402 and several lock disc flanges 202 are used within the locking mechanism 116. Lock disc flanges 202 are arranged in a space between one or more lock disc cams 302. Each lock disc flange 202 includes three openings 204 (or at least two) arranged 90 degrees apart that act as clearance holes for receiving the protrusions 406 of the key 402. In this way, each opening 204 of the one or more lock disc flanges 202 is configured to slidably receive one of the one or more protrusions 406 of the key 402. The lock disc flanges 202 restrict rotation of the key 402 when one of the protrusions 406 of the key 402 aligns with and engages one of the interior faces 206 of the lock disc flange 202.

Figure 3:
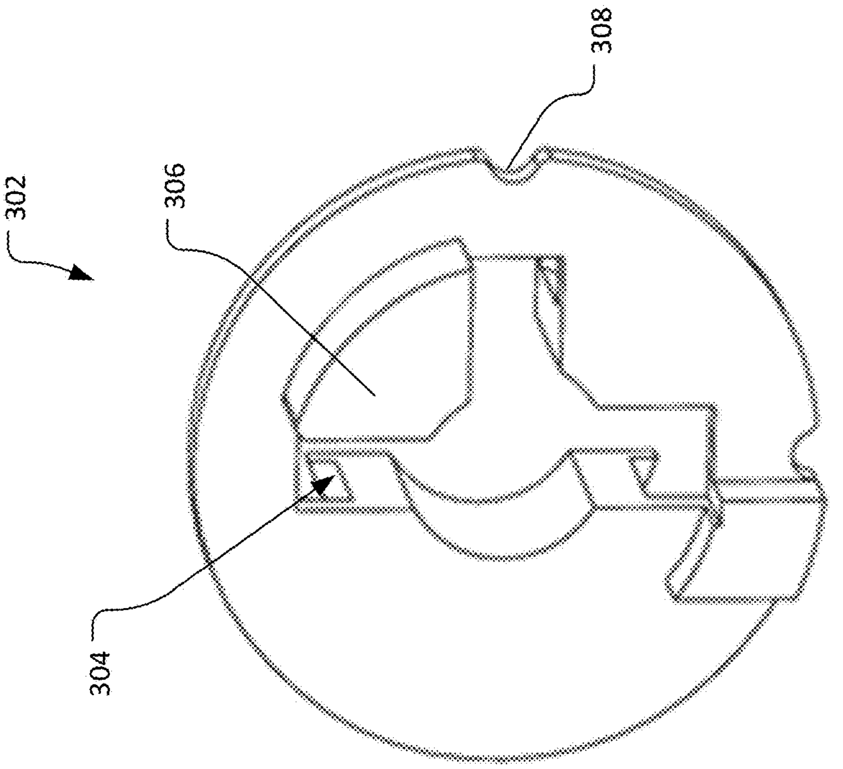
FIG. 3 is a perspective view of a lock disc cam for the locking mechanism.

The lock disc flange 202 is receivable by openings within the body 104*a* and cover 104*b* to capture the lock disc flange 202 within the clamshell housing 104. At least two recesses 208 arranged 90 degrees apart along the outer circumference of the lock disc flange 202. In other words, each lock disc flange 202 comprises at least two recesses 208 arranged at different angles along an outer circumference of the each lock disc flange 202. The recesses 208 engage with compatible protrusions of the clamshell housing 104 to rotationally lock the lock disc flange 202 once the locking mechanism 116 is set for initial use, which will be explained in further detail below. FIG. 3 is a perspective view of a lock disc cam 302 for the locking mechanism 116. Lock disc cams 302 are used to control which key 402 and which pattern of protrusions 406 can be used to unlock the locking mechanism 116. Lock disc cams 302 include openings 304 that substantially correspond to the openings 204 of the lock disc flanges 202. In this way, a series of openings 204 of the lock disc flanges 202 and the series of openings 304 of the lock disc cams 302 provide a space for the key 402 to be fully inserted into the locking mechanism 116. In this way, each opening 304 of the one or more lock disc cams 302 is configured to slidably receive one of the one or more protrusions 406 of the key 402.

When the key 402 is fully inserted, the protrusions 406 are aligned with respective interlocking tabs 126*a* of the body 104*a* or are aligned with cam features 306 of a series of lock disc cams 302, depending on the orientation of the respective protrusion 406 of the key 402. The cam feature 306 protrudes along a centerline of the lock disc cam 302.

At least two recesses 308 arranged 90 degrees apart along the outer circumference of the lock disc cam 302. In other words, each lock disc cam 302 comprises at least two recesses 308 arranged at different angles along an outer circumference of the each lock disc cam 302. The recesses 308 engage with compatible protrusions of the clamshell housing 104 to rotationally lock the lock disc cam 302 once the locking mechanism 116 is set for initial use, which will be explained in further detail below. In this way, each lock disc cam 302 is rotatable before encoding the catheter lock system 102 with the key 402 and not rotatable after encoding the catheter lock system 102 with the key 402.

When the catheter lock system 102 is closed, it is locked using the five interlocking tabs 126*a*, 126*b* protruding from the body 104*a* and the cover 104*b* that engage each other. Once engaged, these locking locations are released using the key 402 depending on the position of protrusions 406 which line up with the interlocking tabs 126*a*, 126*b* at each locking location.

On initial use, the cover 104*b* is closed and then opened by the key 402 to set the locking mechanism 116. Although only one locking tab location is required to secure the catheter lock system 102 in the closed configuration, when first closed, all locking locations (i.e., all interlocking tabs 126*a*, 126*b*) engage to secure the cover 104*b* to the body 104*a*. The key 402 is then inserted to set (or encode) the lock. The flat surface of each protrusion 406 of the key 402 is arranged at a second angle and configured engage a respective sidewall of the respective one or more interlocking tabs of the body 104*a*. In other words, the locking mechanism 116 of the catheter lock system 102 is configured to be encoded with the key 402 upon an initial rotation of the key 402 within the locking mechanism 116.

When the key 402 is rotated 90 degrees, each protrusion 406 located along a top surface of the key 402 interacts with a respective interlocking tab 126*a* from the body 104*a* to release the engagement of these protrusions 126*a* with the protrusions 126*b* of the cover 104*b* at that specific location. In other words, the flat surface of each protrusion 406 of the key arranged at a first angle (e.g., each protrusion 406 on the top of the key 402) is configured engage a respective sidewall of the respective one or more interlocking tabs 106*b* of the body. Hence, a rotation of the key 402 is operable to cause the interlocking tabs 126*a* of the body 104*a* to release from the compatible interlocking tabs 126*b* of the cover 104*b* using each of the one or more protrusions 406 of the key 402.

Each protrusion 406 of the key 402 located along a side face of the key 402 interacts with respective cam features 306 of the lock disc cams 302 located at that location. This engagement rotates the lock disc cam 302 so that the opposite side of the cam feature 306 engages with the interlocking tabs 126*a* from the body 104*a* to release it from the cover 104*b* at that specific location. In other words, the flat side face of each protrusion 406 of the key 402 arranged at a second angle (e.g., each protrusion 406 on the side of the key 402) is configured engage the respective cam features 306 of the respective lock disc cams 302.

In this way, each interlocking tab 126*a* of the body 104*a* is released either by direct interaction with a protrusion 406 from the top of the key 402 or by the cam feature 306 interacting with a protrusion 406 from the side of the key 402. When each of the interlocking tabs 126*a*, 126*b* are released, the locking mechanism no longer locks the catheter lock system 102 in the closed configuration, so the cover 104*b* can be opened. Once the lock is released, the cover 104*b* can be opened manually by hand. However, some implementations use a torsional spring to force the cover 104*b* open once the lock is released.

The key 402 is then rotated back 90 degrees and removed from the locking mechanism 116. Lock disc cams 302 located at the engagement locations with key protrusions 406 to the side have rotated to interact with the interlocking tabs 126*a* from the body 104*a* and do not rotate back to their original position. These rotated lock disc cams 302 discs remain engaged with the interlocking tabs 126*a* from the body 104*a* preventing the interlocking tabs 126*a* from engaging with the complementary interlocking tabs 126*b* from the cover 104*b*. This means that these locations no longer lock when the cover 104*b* is closed.

At locations where the key protrusions 406 are along the top, the lock disc cams 302 do not rotate and the interlocking tabs 126*a* at these locations continue to interact and lock the body 104*a* to the cover 104*b*. The lock disc cams 302 are locked in place by the action of the initial key rotation. The lock mechanism 116 is now set to the specific key protrusion 406 pattern. When the cover 104*b* is again closed and locked only a key 402 with the same pattern of protrusions 406 will unlock the catheter lock system 102.

Figure 4:
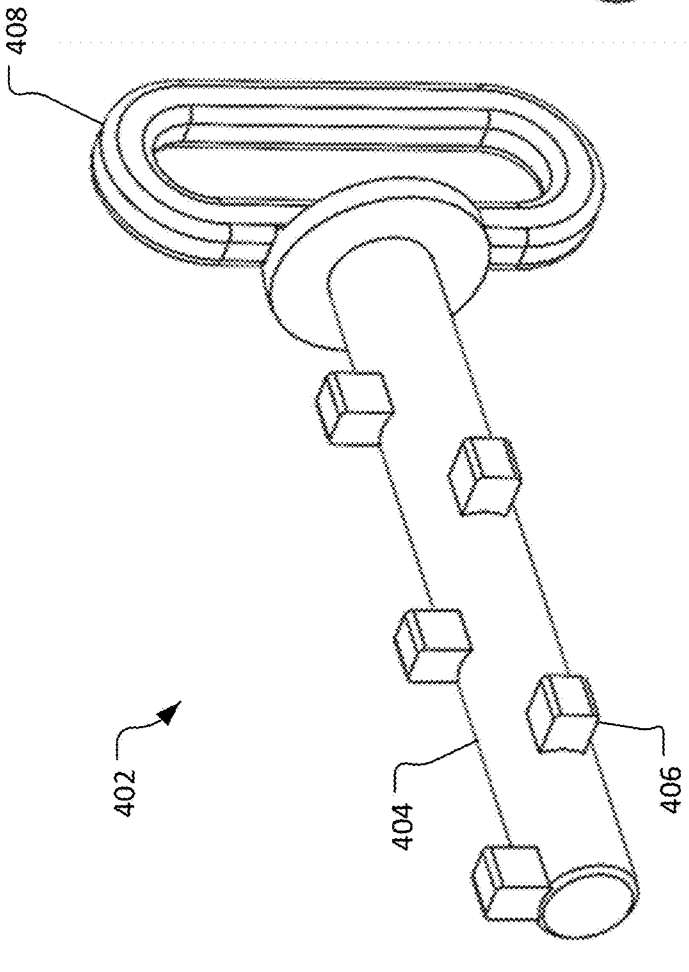
FIG. 4 is an isometric view of a key for the locking mechanism.

FIG. 4 is an isometric view of the key 402. A cylindrical shaft 404 extends along a central axis of the key 402 and defines the locations of the protrusions 406. The key 402 includes one or more protrusions 406 on both a side face and a top face as previously described. In other words, the one or more protrusions 406 are arranged at two different angles along a circumference of the shaft 404 of the key 402 such that some are on the top and some are on the side. The two different angles are 90 degrees apart.

The protrusions 406 are rectangular and each protrusion has a flat surface for engagement with either the cam features 306 of the lock disc cams 302 or a sidewall of the interlocking tabs 126*a*. The protrusions 406 are equally spaced to correspond with the spacing of the interlocking tabs 126*a*, 126*b*. The key 402 also includes a grip 408 for holding the key 402.

Figure 5:
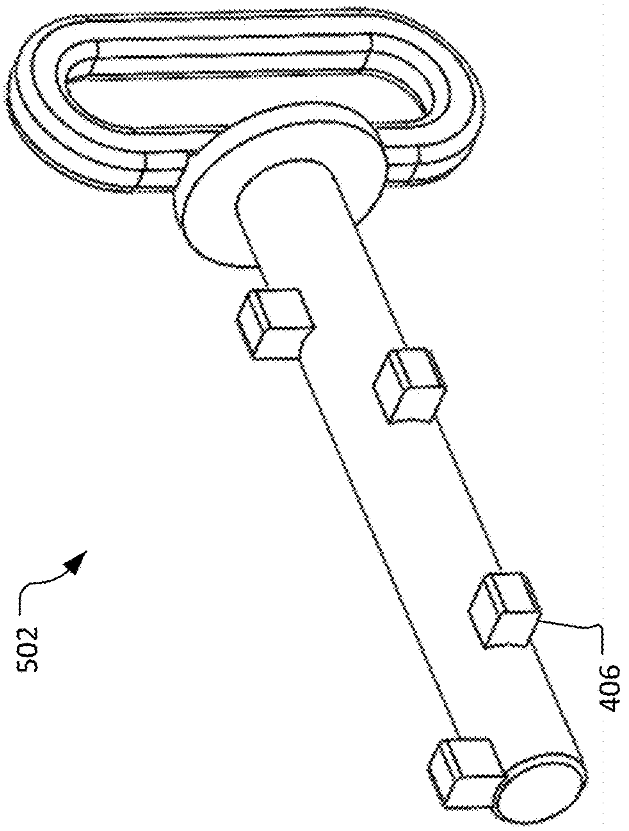
FIG. 5 is an isometric view of a key with variable pawls for the locking mechanism.

FIG. 5 is an isometric view of a key 502. Key 502 is substantially similar to key 402 but includes a different pattern of protrusions 406. Key 502 includes four protrusions 406.

If key 502 is inserted into the locking mechanism 116 that was set (or encoded) to key 402, then the lock will not open. This is because each of these keys 402, 502 have a different pattern of protrusions 406. If a protrusion 406 is moved from the side of the key 402 to the top of a modified key, the modified key will not be able to rotate in the locking mechanism 116 because the lock disc cam 302 at that respective location would prevent rotation of the modified key. This is because the lock disc cam 302 was previously moved and set (or encoded) by the key 402.

Similarly, if a protrusion 406 is moved from the top of the key 402 to the side of a modified key, rotation will be blocked by the lock disc cam 302 still in its original rotational position. Thus, each catheter lock system 102 can be individualized to a specific key.

A number of possible keys is equal to $2^X-2$, where X is the number of protrusions 406 (read as 2 to the power X minus 2). Furthermore, keys should not have all the protrusions 406 on the top or all on the side. For example, for the illustrated implementation with 5 interlocking tab 126*a*, 126*b* locations, the number of unique keys is 30.

Figure 6B:
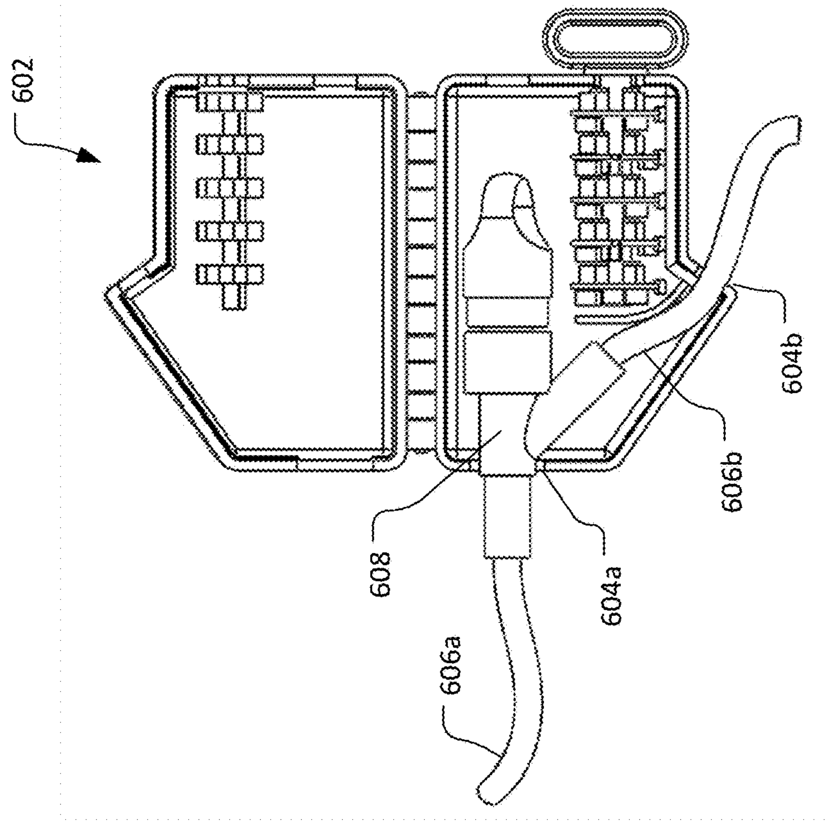
FIGS. 6A-6F are views of a protective clamshell with two ports in a "Y" configuration.
Figure 6A:
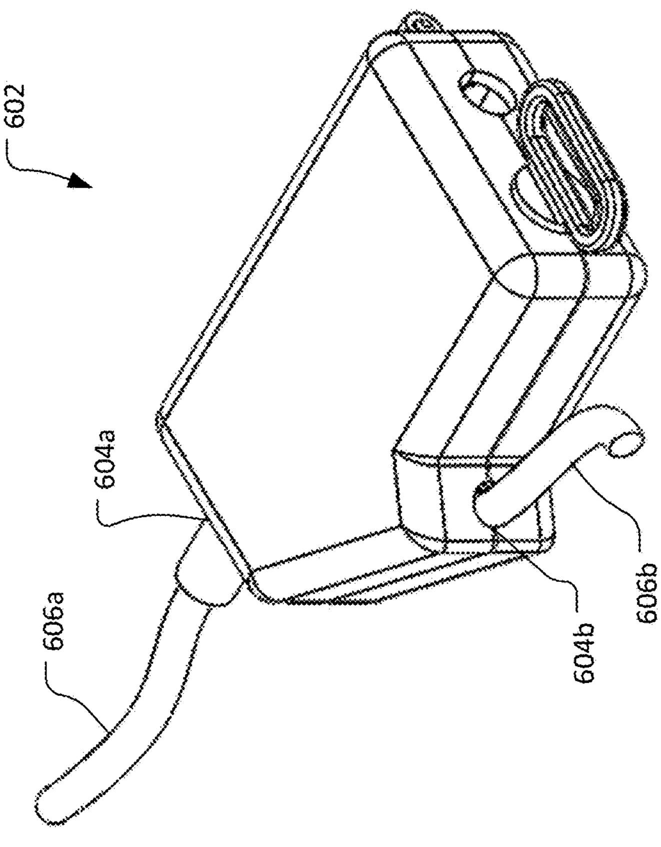

FIGS. 6A and 6B are views of a catheter lock system 602. Catheter lock system 602 is substantially similar to catheter lock system 102, except the catheter lock system 602 is configured with a "Y" access port defined by the access ports 604*a*, 604*b* instead of the single access port 110 of catheter lock system 102. The "Y" access port enables an IV catheter line 606*a*, 606*b* with a "Y" port 608 to pass through the catheter lock system 602 to either another catheter lock system 602 or to a second port (not shown) for injecting additional medicine. The IV catheter has two lines, line 606*a* and line 606*b*. A centerline of the access ports 604*a*, 604*b* of the housing are angled with respect to each other about an angle of 45 degrees so that the lines 606*a*, 606*b* are also about 45 degrees. However, other implementations use other angles (e.g., 0, 30, 60, 90 degrees, etc.).

In other implementations, ports which are protected by the device include a transposition of the line 606*b* and "Y" port 608.

Figure 6C:
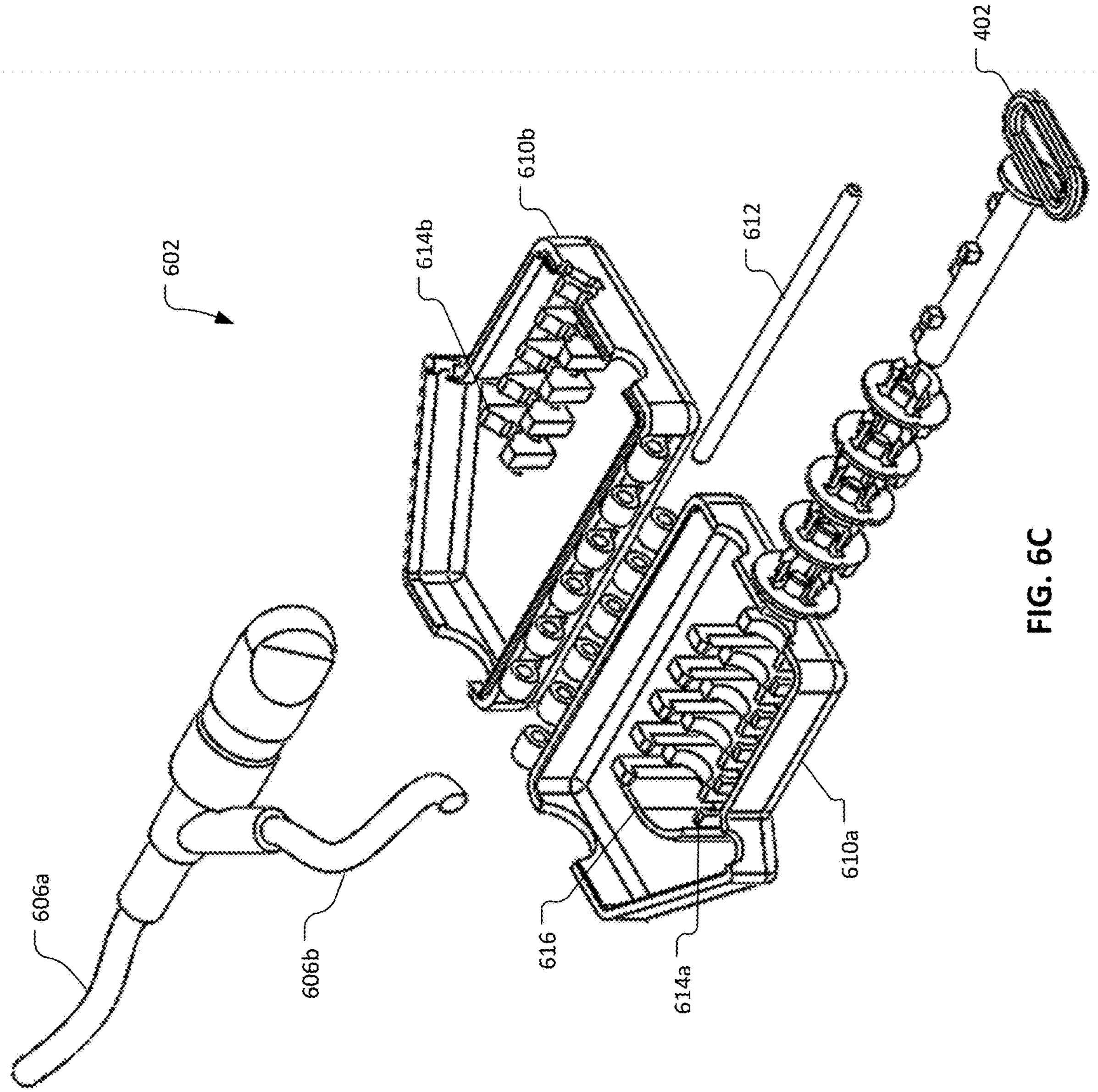

FIG. 6C is an exploded view of the catheter lock system 602. Each component is substantially similar to the components of catheter lock system 102. A clamshell housing with a body 610*a* and a cover 610*b* is hinged along an axis defined by a pin 612. The pin 612 is longer in catheter lock system 602 than the pin 122 of the catheter lock system 102 to accommodate the larger clamshell housing needed for the "Y" port.

A series of interlocking tabs 614*a* on the body 610*a* engage with a series of interlocking tabs 614*b* on the cover 610*b*. A shield feature 616 protects line 606*b* of the IV catheter from being damaged by the key 402. In other words, the shield feature 616 is configured to protect the key 402 from damaging the IV catheter. The shield feature 606 protrudes from an inside face of the body 610*a* and is curved to accommodate the 45 degree angle of the access ports 604*a*, 604*b*.

Figure 6D:
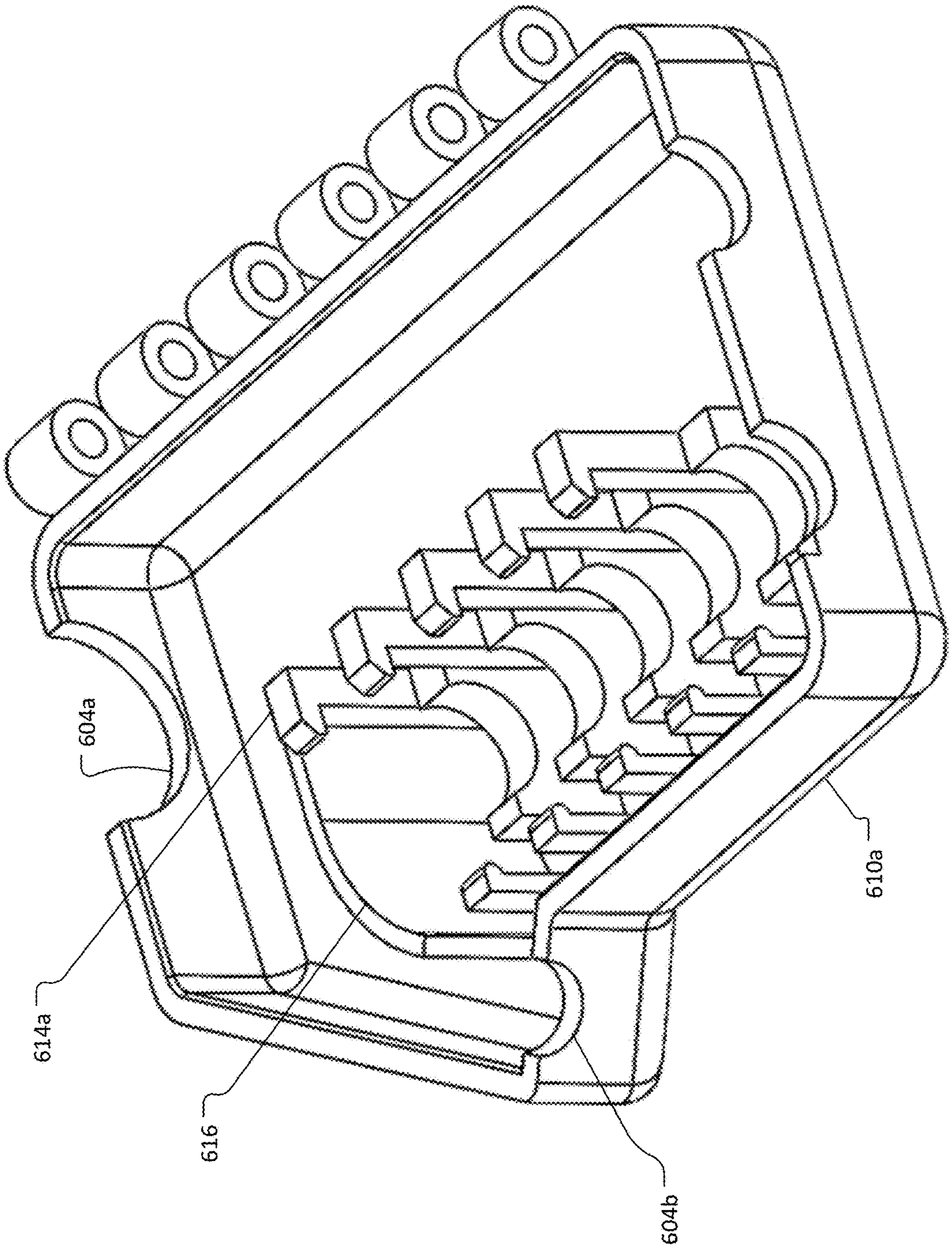

FIG. 6D is a perspective view of the body 610*a*.

Figure 6E:
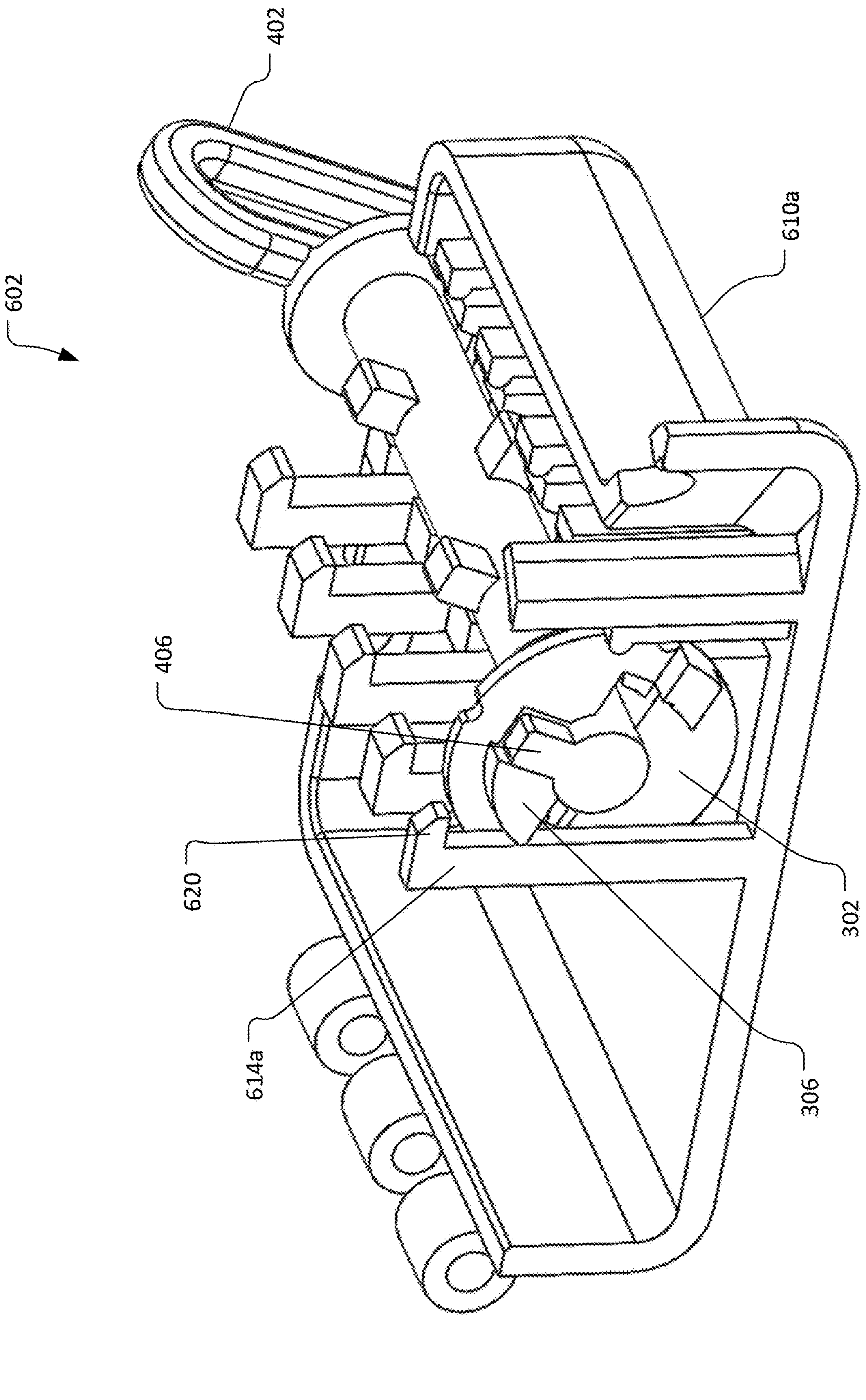

FIG. 6E is a cross section view of the catheter lock system 602 showing detail of a cam feature 306 of a lock disc cam 302 that is engaging an interlocking tab 614*a* on the body 610*a*. The interlocking tab 614*a* includes a hook feature 620.

When the key 402 is turned, the cam feature 306 engages the interlocking tab 614*a* to bend the interlocking tab 614*a* such that it no longer engages with a compatible interlocking tab 614*b* of the cover 610*b*. This action releases the lock at this location, but depending on the lock locations, releasing one interlocking tab 614*a* may not be sufficient to release the lock entirely. For example, if at least one other interlocking tabs 614*a* is still engaged with a compatible interlocking tab 614*b* of the cover 610*b*, the lock will not be released and the cover 610*b* will not open.

Figure 6F:
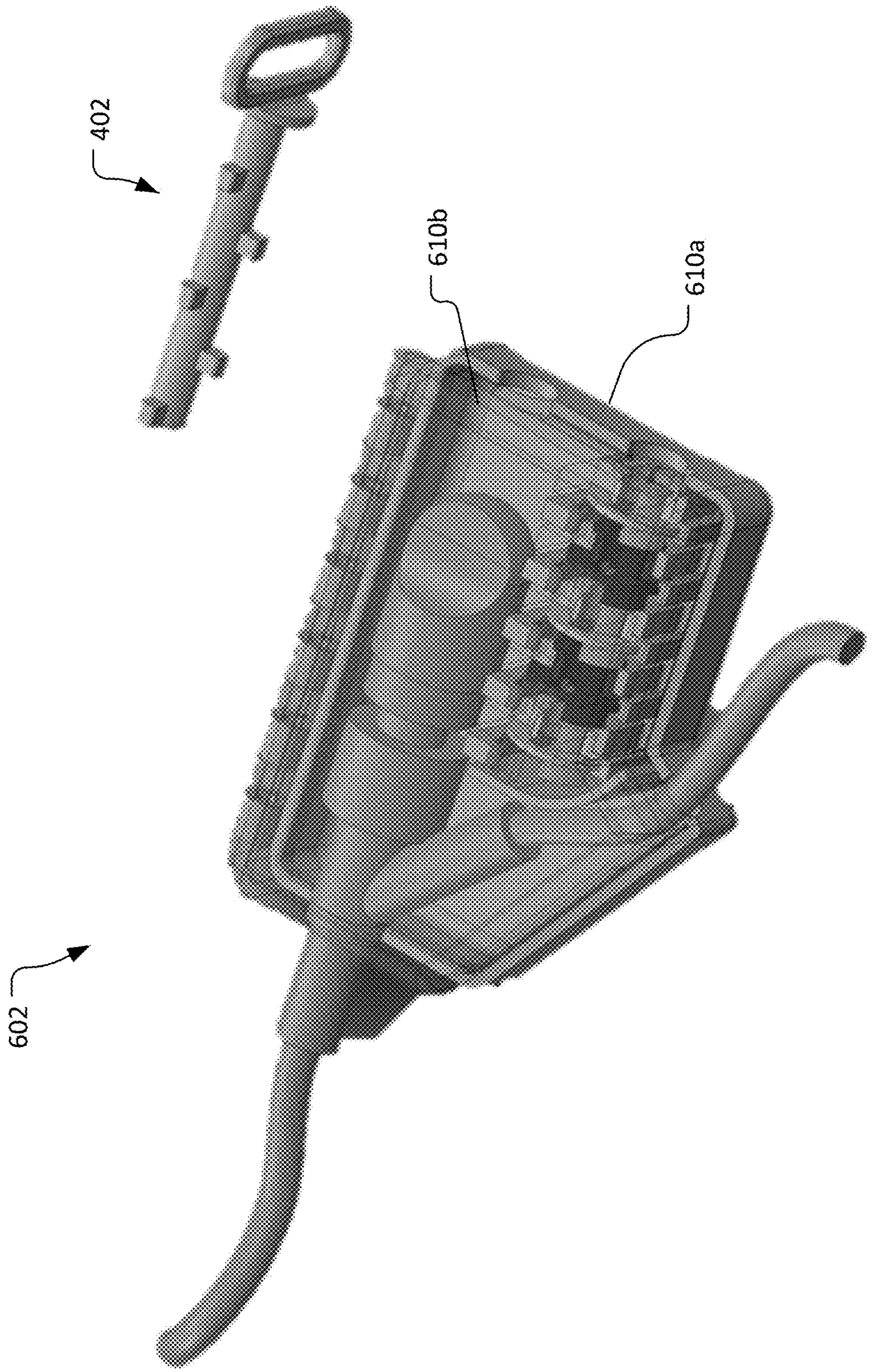

FIG. 6F is a rendering of the catheter lock system 602 showing the cover 610*b* in a translucent state so it is see-through. The engagement of the interlocking tabs 614*a* of the body 610*a* with the interlocking tabs 614*b* of the cover 610*b* is illustrated.

Figure 7A:
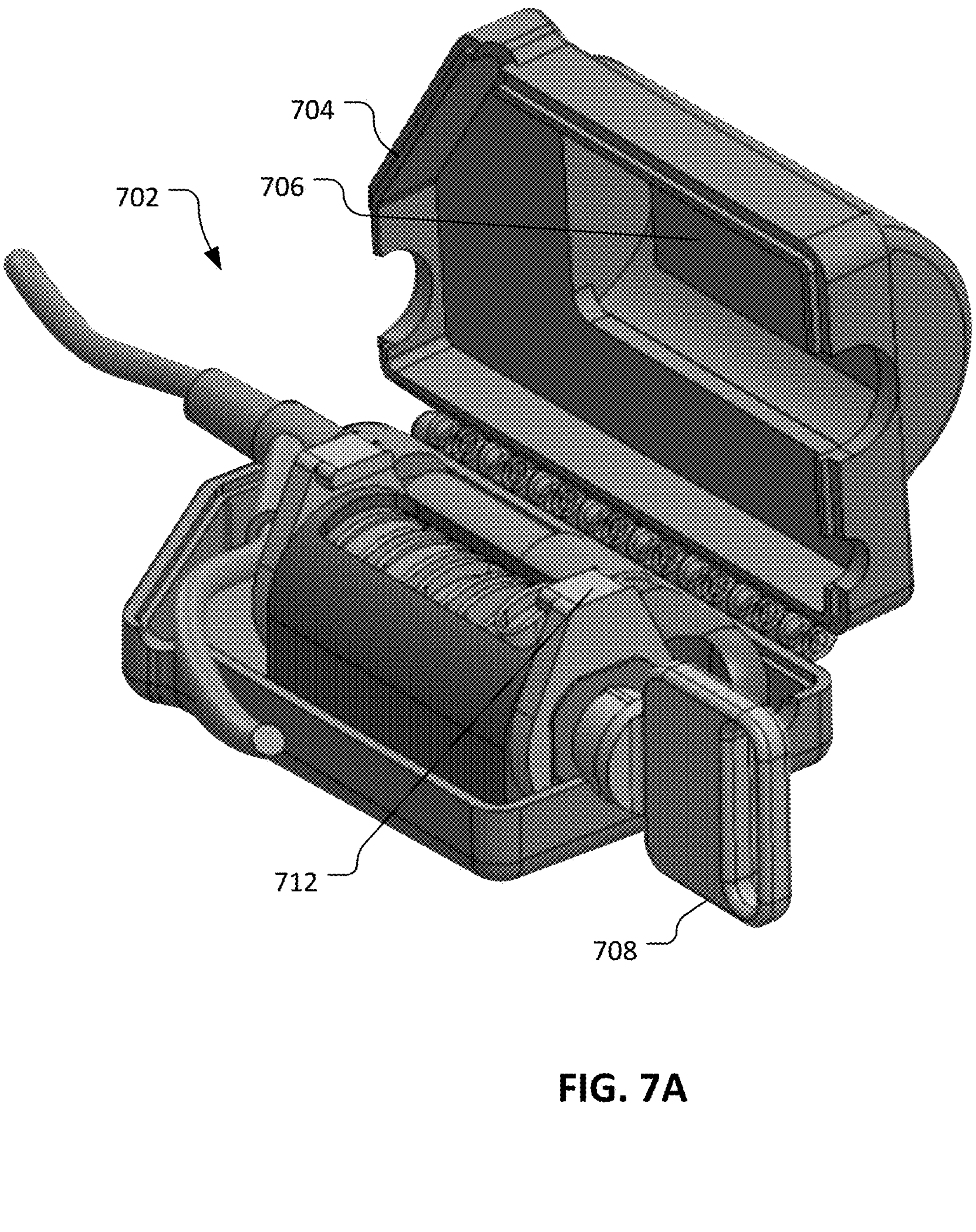
FIGS. 7A and 7B are views of a protective clamshell that uses a wafer locking mechanism.
Figure 12A:
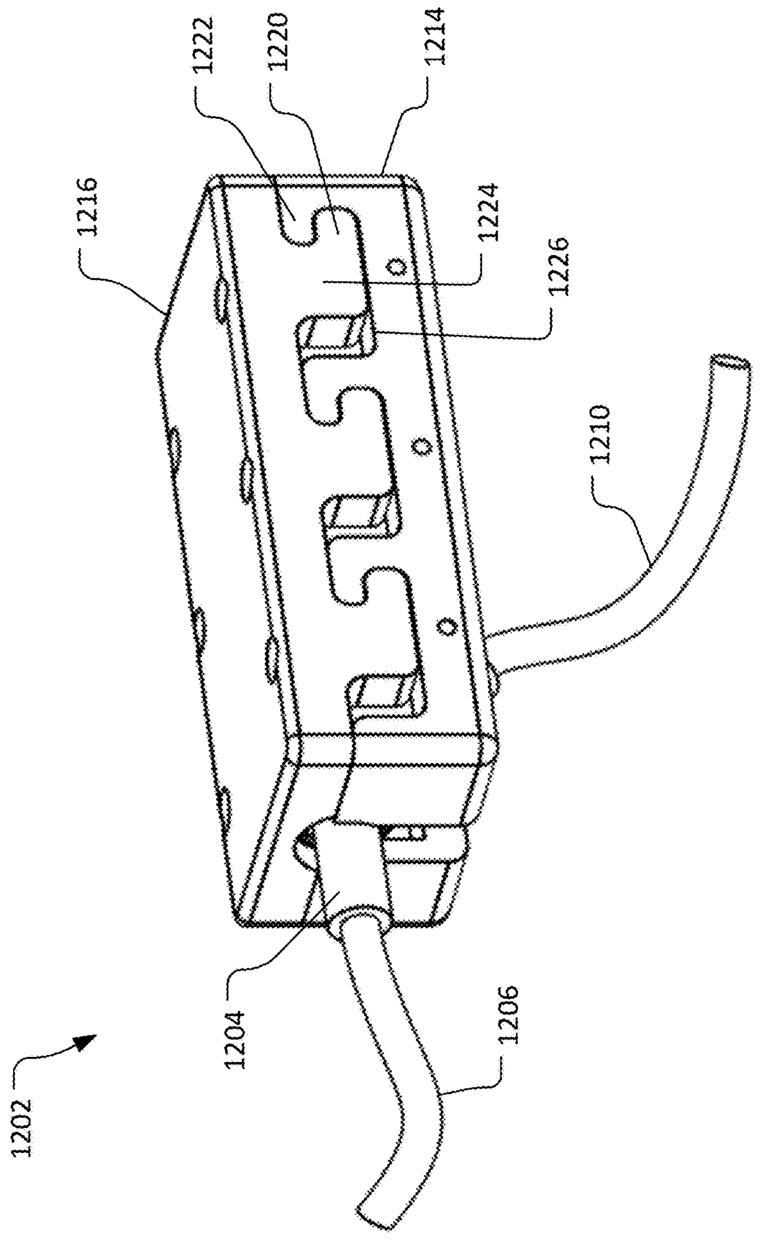
FIGS. 12A-12D show perspective views of a catheter lock system that includes a sliding locking mechanism.

While the locking mechanisms described above use a cam and lock disc mechanism, other locking mechanisms can also be used. For example, FIG. 7A illustrates a wafer locking mechanism and FIG. 12A illustrates a sliding locking mechanism. These mechanisms are described in further detail below.

Figure 7B:
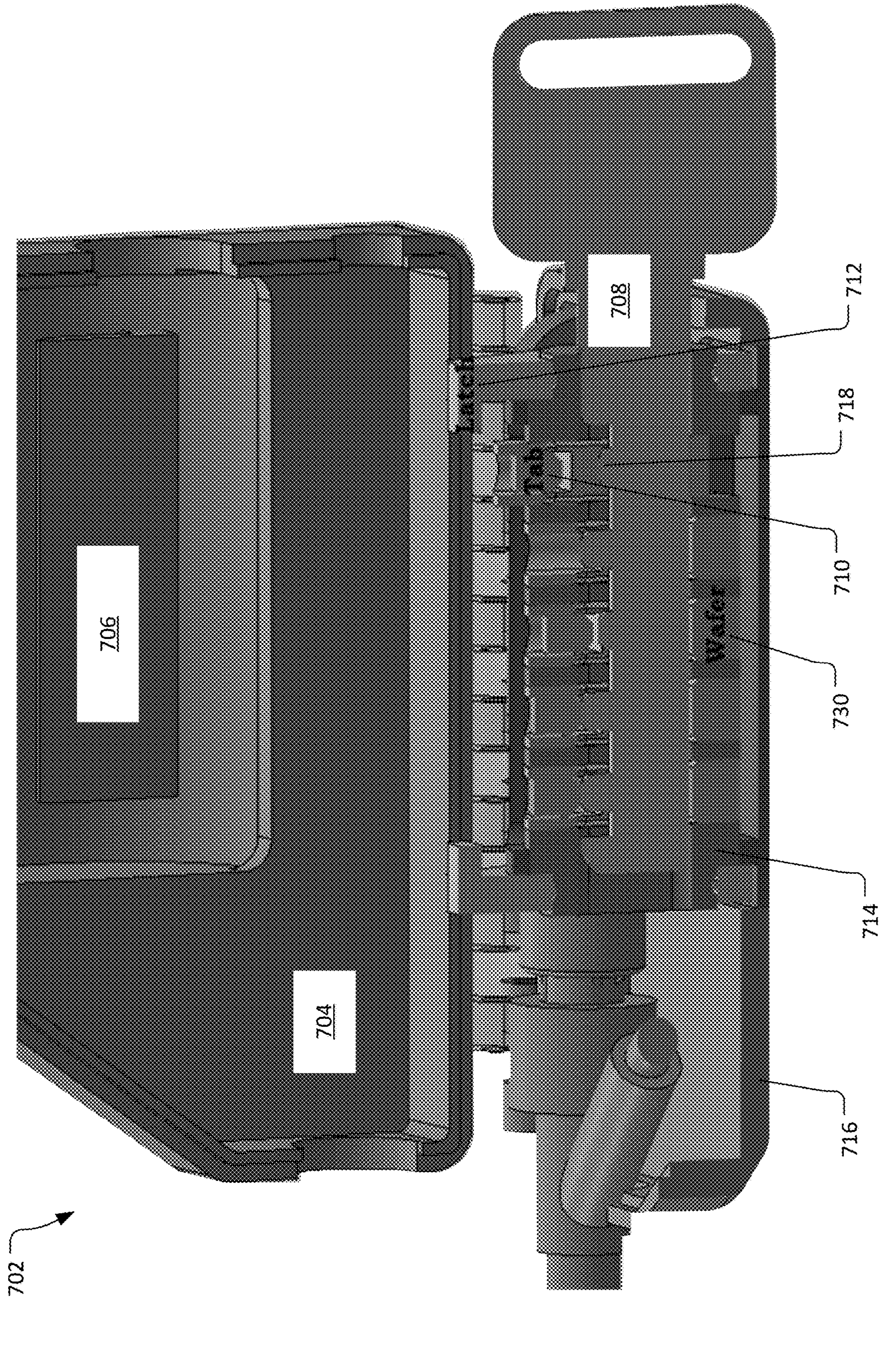

FIGS. 7A and 7B are views of a catheter lock system 702 that includes a wafer tumbler locking mechanism. FIG. 7A is a perspective view of the catheter lock system 702 in the open configuration and FIG. 7B is a perspective cross-section view of the catheter lock system 702 in the open configuration. The cut plane for the cross-section view is through the center of a key 708 when the key 708 in inserted into the catheter lock system 702.

The catheter lock system 702 is similar to the catheter lock system 602 except the locking mechanism in the catheter lock system 702 is implemented as a wafer tumbler system. Like the catheter lock system 602, the catheter lock system 702 includes a cover 704 and a base 716 pivotably connected on a hinged axis. The cover 704 includes a cover tab 706 recessed within the cover 704. The cover tab 706 engages a two latches 712 to lock the catheter lock system 702. For example, when the two latches 712 rotate about an axis of a key 708 (e.g., during an unlocking procedure as described below), the latches 712 disengage with the cover tab 706 allowing the cover 704 to pivoted open from the base 716.

The catheter lock system 702 includes a cylinder 714 that includes the two latches 712 and houses a plurality of wafers 730. Each wafer 730 includes a tab 710 that engages respective protrusions 718 of the key 708. The wafers 730 are able to be set (or encoded) to a specific key 708 by moving the settable tab 710 embedded into each wafer 730.

Figure 8B:
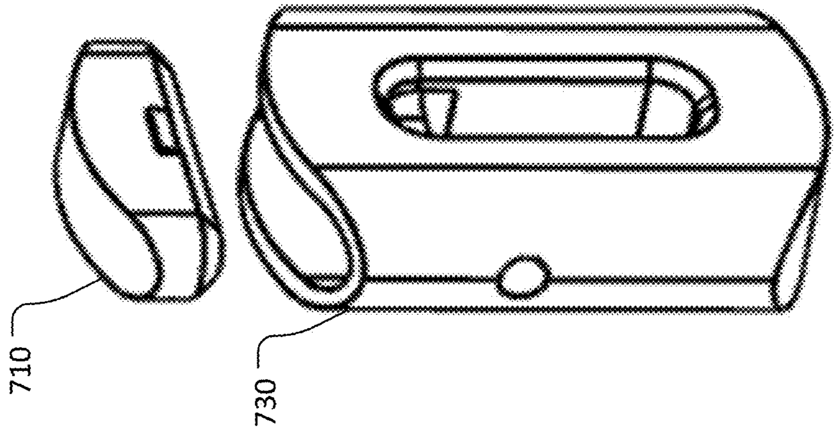
FIGS. 8A and 8B are perspective views of a wafer for use in the locking mechanism of FIGS. 7A and 7B.
Figure 8A:
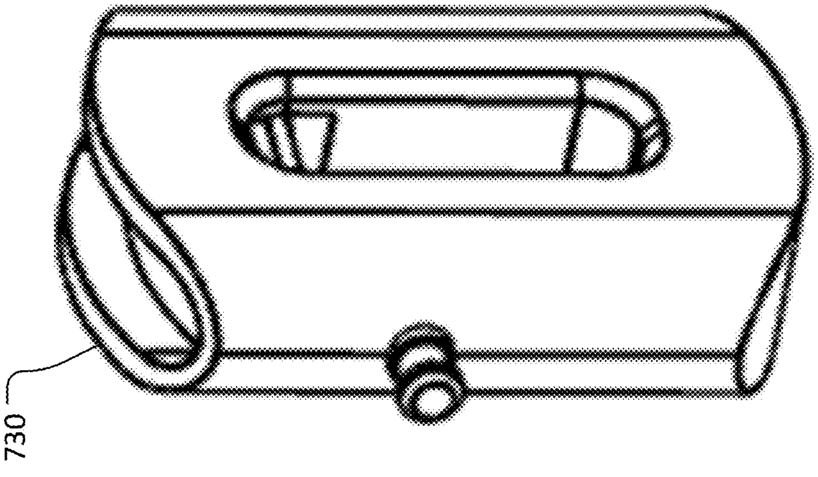
Figure 9:
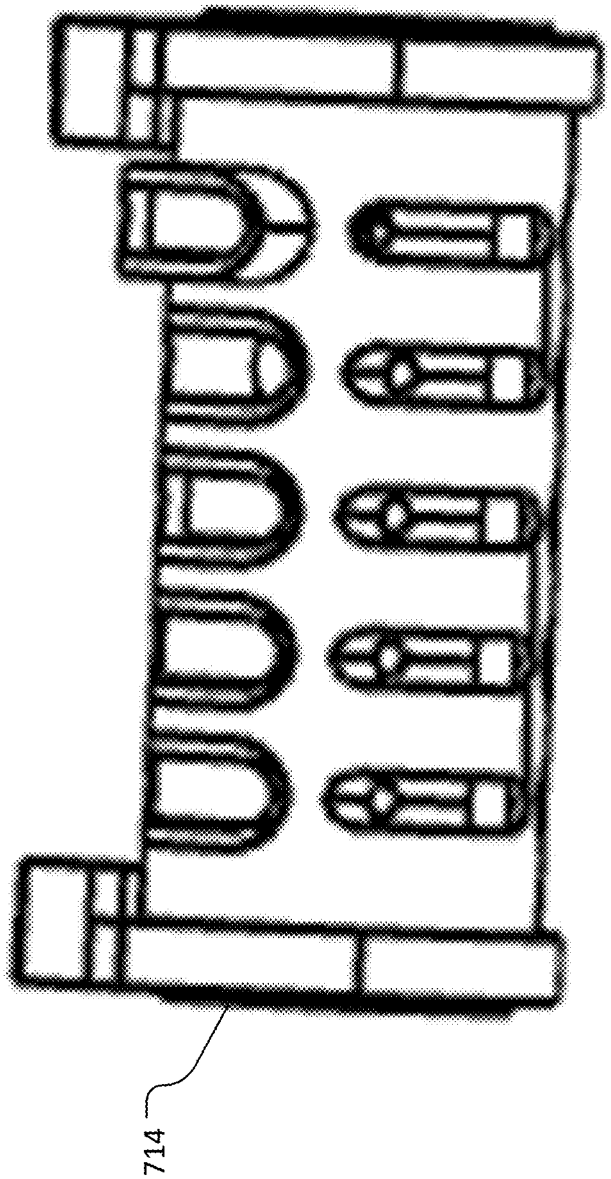
FIG. 9 is a perspective view of a cylinder with wafers installed for use with the locking mechanism of FIGS. 7A and 7B.

FIGS. 8A and 8B show the wafer 730 and tab 710 in further detail and FIG. 9 shows a perspective view of the cylinder 714 with the wafers 730 installed. When the specific pattern of wafers 730 matches the specific pattern of protrusions 718 on the key 708, the cylinder 714 is able to rotate (e.g., under the action of a user rotating the key 708) causing the two latches 712 rotate to disengage a tab 706 on the cover 704. This disengagement causes the catheter lock system 702 to unlock as described above. As described above, it can be advantageous to have numerous catheter lock systems encoded to the same protrusion pattern so that many keys can be fabricated and distributed throughout an institution (such as a hospital) for use with any of the catheter lock systems. This allows a single key encoding to be used for all catheter lock systems.

Figure 10:
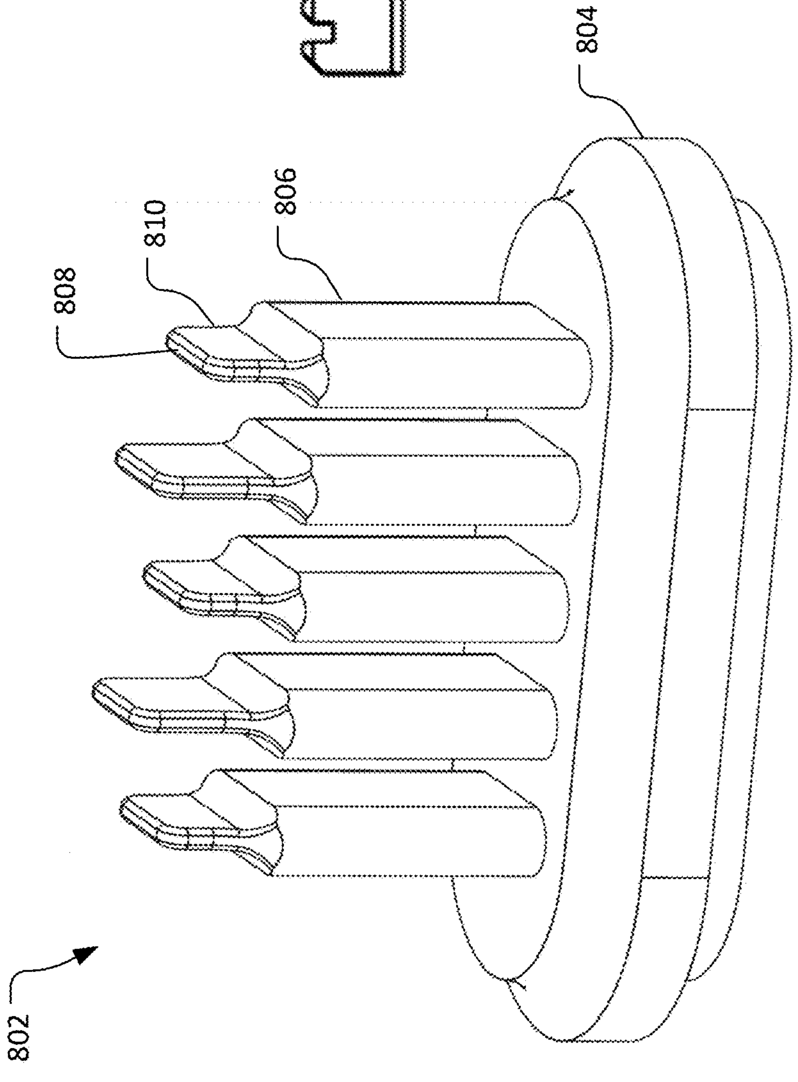
FIG. 10 is a perspective view of a setting device for use with the locking mechanism of FIGS. 7A and 7B.

FIG. 10 shows a setting device 802 for use with the catheter lock system 702. In some examples, the setting device 802 is used at time of catheter lock system 702 placement to set the catheter lock system 702 to the pattern of protrusions 718 of institution specific key 708. Setting the catheter lock system 702 to the pattern of protrusions 718 is accomplished by pressing the setting device 802 onto the cylinder 714 thereby depressing a specific pattern of tabs 710 into a "down" position. In this example, "down" means closer to the axis of the key 708 and "up" means further away from the axis of the key 708. Once the setting device 802 positions the tabs 710 into the "up" vs. "down" positions, only a key with protrusions that correspond to the pattern of the setting device 802 can be used to unlock the catheter lock system 702.

The setting device 802 includes a base 804 and a plurality of columns 806 each having a contact surface 808 that engages the tabs 710. In this example, the setting device 802 includes five columns 806 to be used to engage five tabs 710, but some setting devices 802 use a different number of columns to engage a different number of tabs (e.g., two columns to engage two tabs, six columns to engage six tabs, etc.). In some examples, the contact surface 808 is located at an end of a recessed section 810 of the column 806. The recessed section 810 enables clearance between the setting device 802 and wafers 730.

Figure 11:
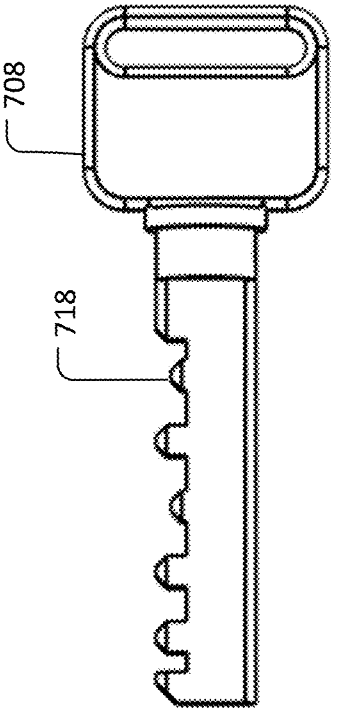
FIG. 11 is a side view of a key for use with the locking mechanism of FIGS. 7A and 7B.

After the catheter lock system 702 is encoded for a specific key 708, catheter lock system 702 cannot be opened by a patient. Generally, a setting device 802 is paired and shipped with each institution specific key 708 so catheter lock systems 702 can be encoded on-site for the specific key 708. In some cases, the catheter lock system 702 is shipped in an open position with all tabs 710 in an "up" position. FIG. 11 shows a side view of the key 708 used with the catheter lock system 702. The key 708 is similar to key 708 but the protrusions 718 are aligned on a single side of the key axis. The protrusions 718 vary in height according to whether the protrusion 718 is configured to engage the tabs 710 in the "down" position vs. in the "up" position.

Figure 12B:
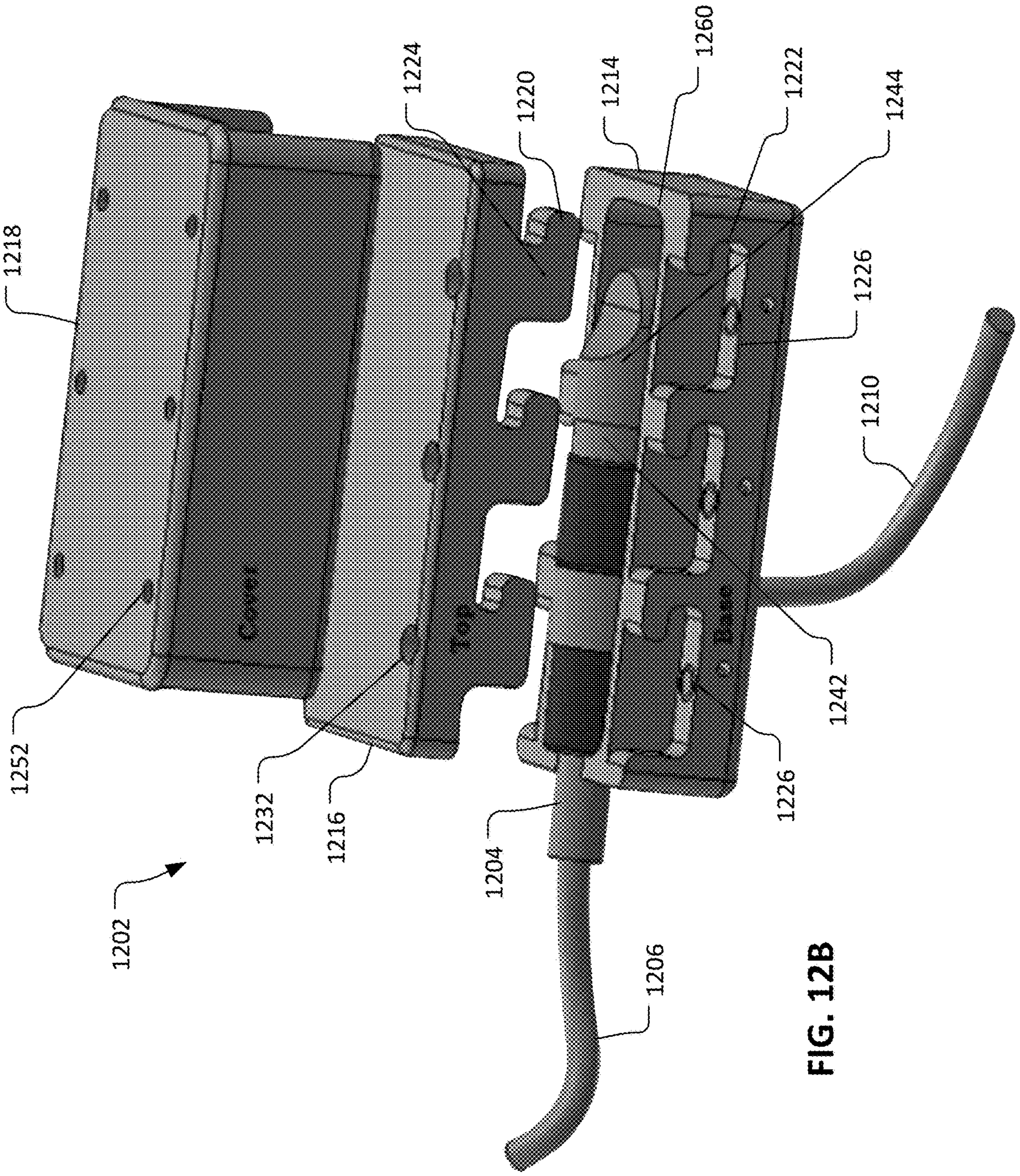
Figure 12C:
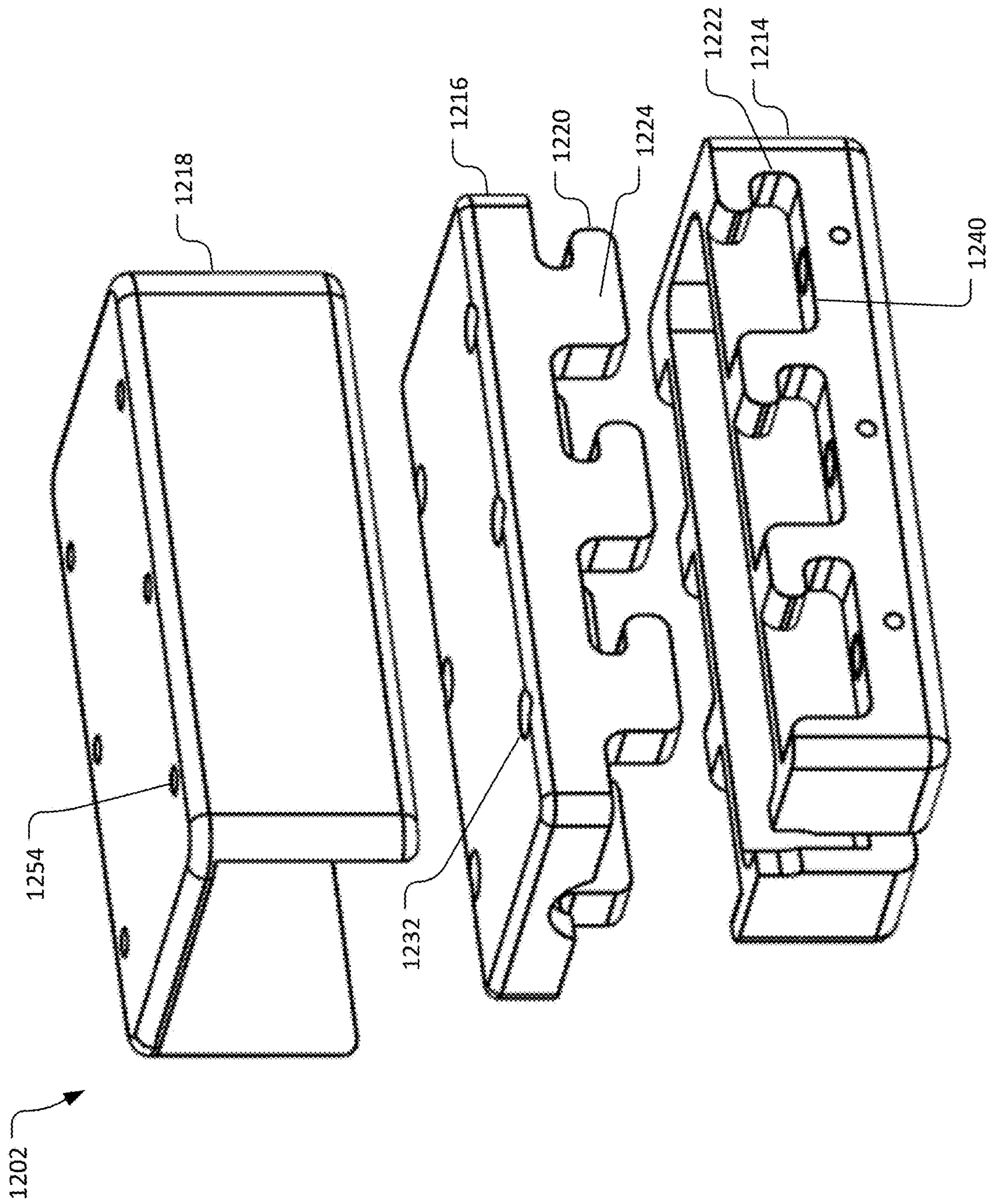
Figure 12D:
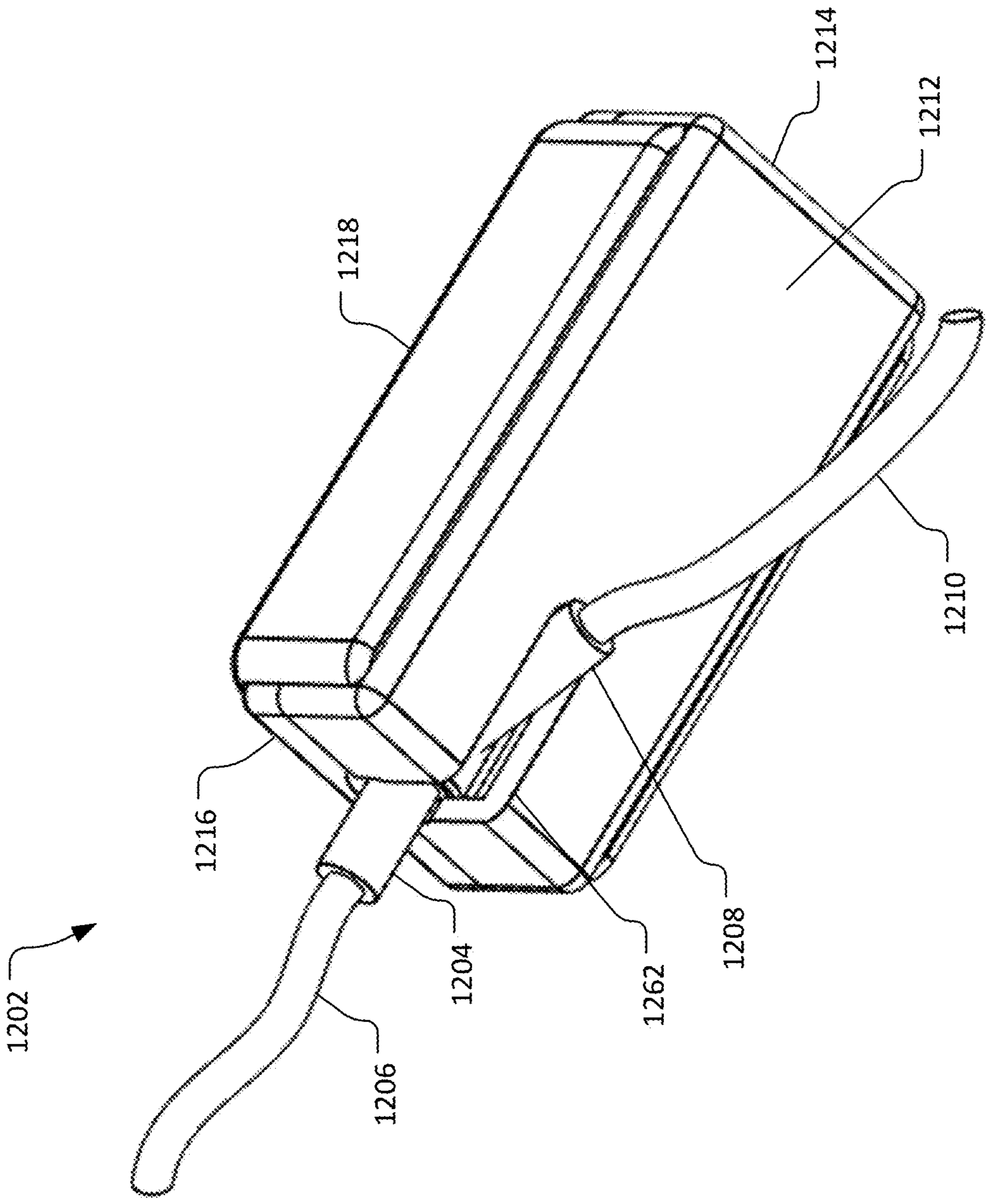

FIGS. 12A-12D show perspective views of a catheter lock system 1202 that includes a sliding locking mechanism. FIG. 12A is a perspective view of the catheter lock system 1202 in a closed configuration. FIG. 12B is a perspective view of the catheter lock system 1202 in an open configuration. FIG. 12C is a perspective view of a base housing 1214, an upper housing 1216, and a cover 1218 of the catheter lock system 1202 in the open configuration. FIG. 12D is a perspective view of the underside of the catheter lock system 1202 in the closed configuration.

The catheter lock system 1202 is similar to the catheter lock system 602 except the locking mechanism in the catheter lock system 1202 is implemented as a sliding locking mechanism and includes a "Y" design different from the catheter lock system 602. As shown in FIG. 12D, the catheter lock system 1202 includes a first access port 1204 with a first catheter line 1206 and a second access port 1208 with a second catheter line 1210. An angle between an axis of the first access port 1204 and an axis of the second access port is between 90 and 135 degrees (e.g., 120 degrees). In this way, the angle represents a "Y" design similar to the catheter lock system 602 except the second access port 1208 extends beyond a bottom surface 1212 of a base housing 1214 of the catheter lock system 1202. The base housing 1214 includes a grooved cut-out 1262 to provide clearance to the first and second access ports 1204, 1208.

The catheter lock system 1202 includes the base housing 1214 and the upper housing 1216. The upper housing 1216 includes a plurality of protrusions 1224 that extend from a body of the upper housing 1216. The plurality of protrusions 1224 engage a plurality of counterpart recesses 1240 in the base housing 1214 so the upper housing 1216 can slide in a direction towards the base housing 1214. Each protrusion 1224 includes a hook protrusion 1220 located on a side of the protrusion 1224. The hook protrusions 1220 are configured to slide into counterpart hook-shaped recesses 1222 of the base housing 1214 so the upper housing 1216 can slide in a direction perpendicular to the direction towards the base housing 1214. In the example shown, the upper housing 1216 is first lowered onto the base housing 1214 and then the upper housing 1216 is slid from left to right to engage the hook protrusions 1220 into counterpart hook-shaped recesses 1222. This engagement closes the catheter lock system 1202.

Figure 13:
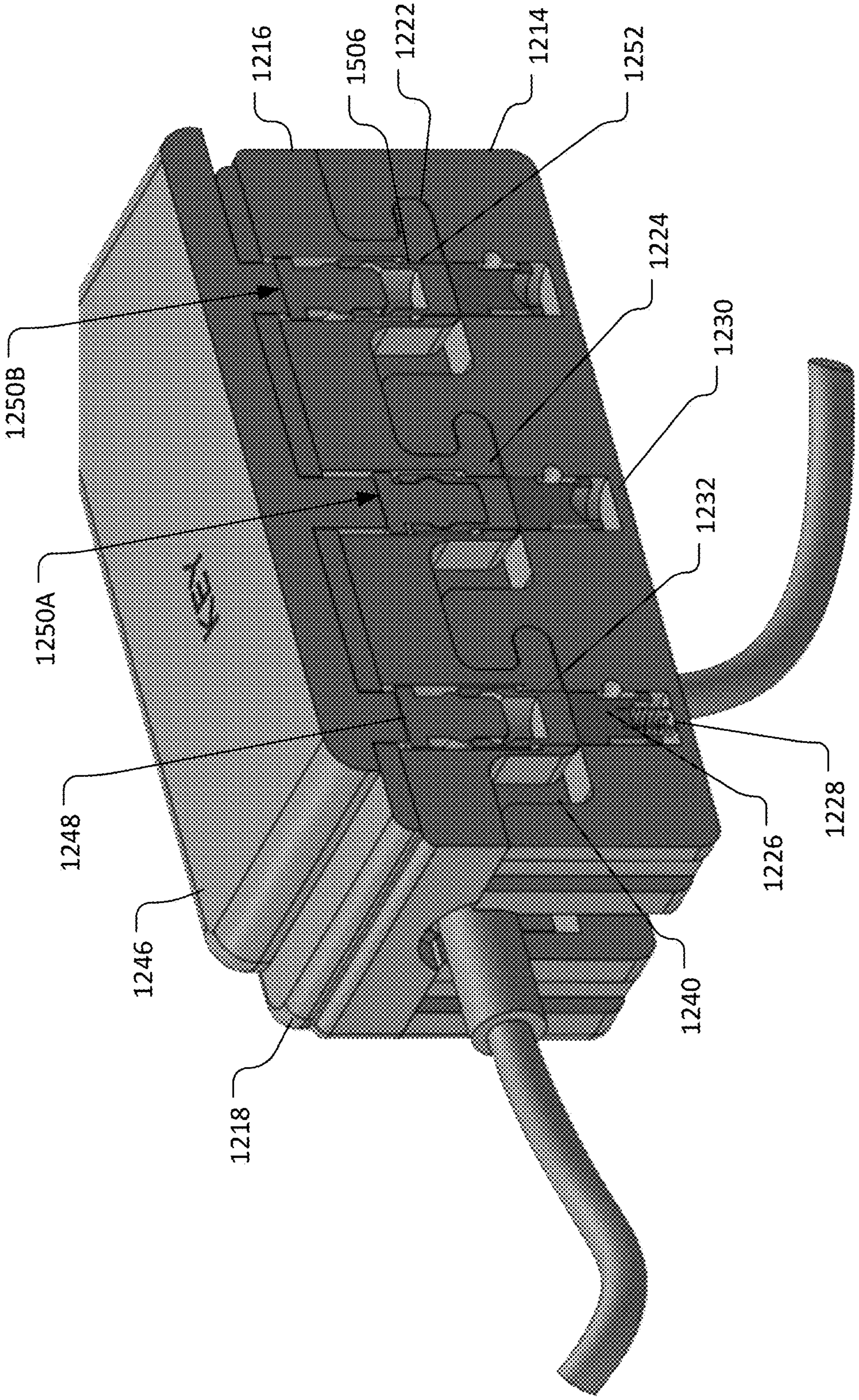
FIG. 13 is a perspective cross-section view of the catheter lock system of FIGS. 12A-12D in the closed and locked configuration.

Referring to FIG. 13, locking the catheter lock system 1202 is accomplished using spring-loaded pins 1226. The base housing 1214 includes a plurality of cylindrical recesses 1230 that house a spring-loaded pin 1226. A spring 1228 biases the spring-loaded pin 1226 in a direction towards the upper housing 1216. The cylindrical recesses 1230 intersect the recesses 1240 so that a spring-loaded pin 1226 projects into each of the recesses 1240. In this way, a user could (e.g., using the users thumb) press the spring-loaded pin 1226 into the recess 1230 and, upon release, the spring-loaded pin 1226 would project out of the recess 1230.

When the upper housing 1216 is first lowered onto the base housing 1214, each protrusion 1224 contacts and pushes a spring-loaded pin 1226 into the cylindrical recess 1230. Then as the upper housing 1216 is slid from left to right relative to the base housing 1214, the hook protrusions 1220 engage into the counterpart hook-shaped recesses 1222 (as shown in FIG. 13). When the hook protrusions 1220 engage into the counterpart hook-shaped recesses 1222, an axis of a cylindrical hole 1232 within the protrusions 1224 aligns with an axis of the cylindrical recess 1230. The diameter of the cylindrical hole 1232 is equal to or greater than the diameter of the cylindrical recess 1230 so that a spring-loaded pin 1226 projects into each cylindrical hole 1232 when the hook protrusions 1220 engage into the counterpart hook-shaped recesses 1222. The projection of the spring-loaded pins 1226 into each cylindrical hole 1232 locks the catheter lock system 1202 and prevents the upper housing 1216 from sliding relative to the base housing 1214.

Figure 16:
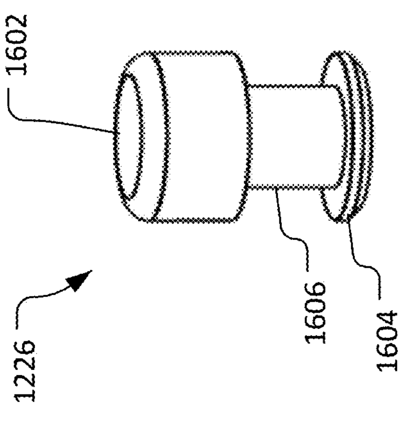
FIG. 16 is a perspective view of a spring-loaded pin for use with the locking mechanism of FIGS. 12A-12D.

FIG. 16 shows details of the spring-loaded pin 1226. The spring-loaded pin 1226 includes a flange 1604 for contacting a spring (e.g., the spring 1228 shown in FIG. 13), a neck region 1606, and a top portion 1602 that protrudes from the cylindrical recess 1230. In some examples, the top portion 1602 is mushroom shaped.

In the closed and locked configuration, the IV catheter port 1242 (shown in FIG. 12B) is closed by a cap 1244 that cannot be removed. This ensures that patients do not tamper with the IV catheter port 1242. For example, when the catheter lock system 1202 is in the open configuration (e.g., as shown in FIG. 12B), a medical professional can remove the cap 1244 and connect the IV catheter port 1242 to a catheter line to provide a drug to a patient connected to catheter line 1206 and/or catheter line 1210. When the catheter lock system 1202 is in the closed and locked configuration (e.g., as shown in FIG. 12A), no one, not even the medical professional can remove the cap 1244. Once the catheter lock system 1202 is locked, a key is required to unlock the catheter lock system 1202. The key is described below with reference to FIGS. 13 and 14. As shown in FIG. 12B, the base housing 1214 includes a central recess 1260 for housing the IV catheter port 1242 and the cap 1244.

Referring back to FIG. 13, each cylindrical hole 1232 houses a pin 1248. The pin 1248 is slidable along the axis of the cylindrical hole 1232 so that the pin 1248 can engage the spring-loaded pin 1226 when urged by a contact force from a key 1246. Each pin 1248 is a two-part design that can be one of two lengths. For example, the pin 1248 can be a first length 1250A or a second length 1250B.

Figure 15:
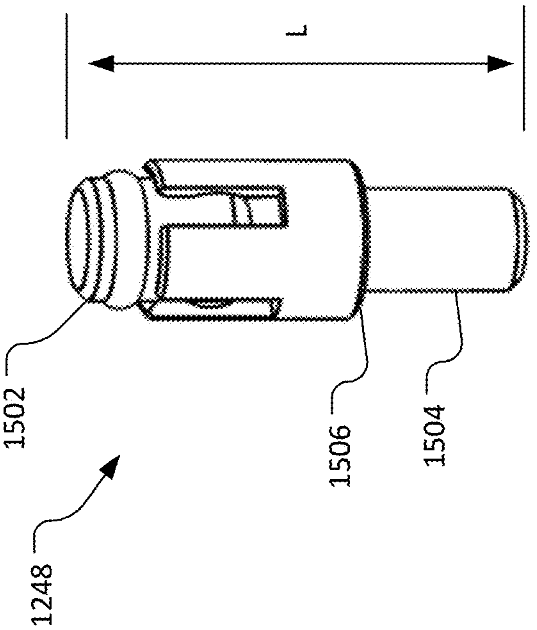
FIG. 15 is a perspective view of an encodable pin for use with the locking mechanism of FIGS. 12A-12D.

FIG. 15 shows details of the pin 1248. The pin 1248 includes a first part 1502 and a second part 1504 that can be slid relative to the first part 1502 to set the pin 1248 to a particular length (L) (e.g., either a first length or a second length). The length of the pin 1248 is measured along the axis of the pin 1248. By varying the pattern of the length of the pins 1248, a specific key is required to unlock the catheter lock system 1202. Generally, the pins 1248 are settable to a long or short position at the time of initial placement.

The pin 1248 includes a flange 1506 that steps the diameter from a first diameter of the first part 1502 to a second, larger, diameter. The flange 1506 is configured to contact a counterpart flange 1252 (shown in FIG. 13) at a travel limit of the pin 1248. The travel limit limits the travel of the pin 1248 in the direction of the spring-loaded pin 1226 so that an incorrect key cannot be used to force the pin 1248 to depress the spring-loaded pin 1226. If an incorrect key were used, the pin 1248 would stop when the flange 1506 engages the flange 1252 and the key would not rest against the cover 1218.

The catheter lock system 1202 includes a cover 1218 that slides over the upper housing 1216 and the base housing 1214. An expanded view of the cover 1218 is shown in FIGS. 12B and 12C. A view of the cover 1218 inserted onto the upper housing 1216 and the base housing 1214 is shown in FIG. 12D. The cover 1218, when inserted on the housing 1216 and the base housing 1214, hides the protrusions 1220, 1224, and recesses 1222, 1240 from view. The cover 1218 includes a plurality of cylindrical holes 1254 that have a smaller diameter than a diameter of the cylindrical holes 1232 of the upper housing 1216. The smaller diameter means that the pins 1248 cannot be removed from the upper housing 1216 once the cover 1218 is installed onto the upper housing 1216 and the base housing 1214 as shown in FIGS. 12D and 13.

Figure 14:
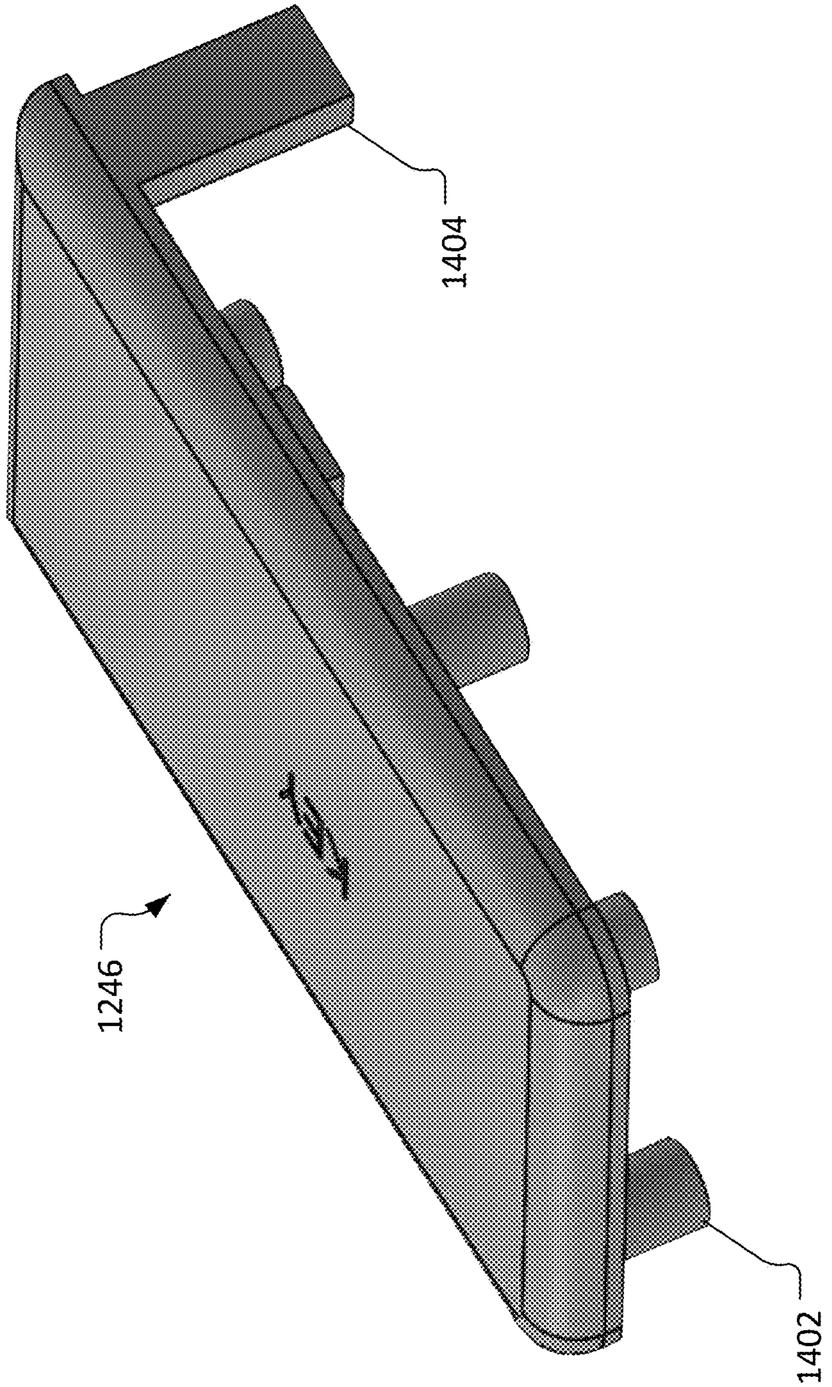
FIG. 14 is a perspective view of a key for use with the locking mechanism of FIGS. 12A-12D.

Referring to FIGS. 13 and 14, the catheter lock system 1202 includes a key 1246. Unlike catheter lock systems 102, 602, and 702, the key 1246 used in the catheter lock system 1202 is a flat plate. The key 1246 includes a planner surface with a plurality of cylindrical protrusions 1402. Each protrusion 1402 has a diameter that is less than or equal to the diameter of the cylindrical holes 1254 of the cover 1218 so the protrusions 1402 extend through the holes 1254 to contact an surface of the first part 1502 of the pin 1248.

As the key 1246 is placed onto the cover 1218, each protrusion 1402 engages and the pins 1248 causing the pins 1248 to retract into the cylindrical recess 1230 of the base housing 1214. Once the key 1246 is fully placed on the cover 1218 (as shown in FIG. 13), each of the pins 1248 are retracted into cylindrical recesses 1230 so that the engagement between the pins 1248 and the protrusions 1224 is released. When the engagement between the pins 1248 and the protrusions 1224 is released, the catheter lock system 1202 is unlocked. A user can then slide the upper housing 1216, the cover 1218, and the key 1246 together in an opposite direction of the locking direction described above to release the engagement between the hook protrusions 1220 and the hook-shaped recesses 1222. Then a user can remove the upper housing 1216, the cover 1218, and the key 1246 from the base housing 1214 thereby opening the catheter lock system 1202.

As shown in FIG. 14, the key 1246 includes a rectangular tab 1404 that is insertable into a counterpart rectangular recess or groove in the cover 1218, the upper housing 1216, and the base housing 1214. In some examples, the groove is located on a side of the cover 1218, the upper housing 1216, and the base housing 1214. The tab 1404 ensures that the key 1246 is oriented properly so that a user cannot flip the key 1246 and try to use the key 1246 in other orientations.

As noted above, the pins 1248 are configurable between a short length and a long length. Generally, the catheter lock system 1202 is shipped with all the pins 1248 in the long position (e.g., as shown by the long position 1250B in FIG. 13). Upon first use of the catheter lock system 1202, the key 1246 is pressed into the upper housing 1216 (e.g., with or without the cover 1218 installed). The specific pattern of protrusions 1402 of the key 1246 are inserted into the specific pattern of holes of the cover 1218, the upper housing 1216, and the lower housing 1214. The specific size and location of the tab 1404 of the key 1246 is also inserted into a counterpart recess or groove.

When the key 1246 is pressed into the upper housing 1216 for the first time, the longer protrusions 1402 engage the pins 1248 first since the catheter lock system 1202 is usually shipped with all the pins 1248 in the long position. Continued pressing of the key 1246 onto the upper housing 1216 causes the longer protrusions 1402 of the key 1246 to force those pins 1248 into the short position. This occurs because the pins 1248 slide toward the base housing 1214 until the flanges 1506, 1252 engage thereby limiting further travel of the pin 1248 in a direction toward the base housing 1214. Any further force in that direction essentially toggles the pins 1248 associated with longer protrusions 1402 from a long configuration to a short configuration (e.g., as shown by the short length 1250A in FIG. 13). In some cases, this forcing action by the user requires more force than needed for routine opening of the catheter lock system 1202. At the same time when the pins 1428 toggle into the short position, the shorter protrusions 1402 of the key 1246 engage the remaining pins 1248. At this point, the key 1246 can be removed because the catheter lock system 1202 has been encoded to that particular key 1246. The catheter lock system 1202 is now ready for use Another feature of the catheter lock system 1202 is that a gap exists between the two flanges 1506, 1252 (e.g., as shown in FIG. 13), when the spring-loaded pins 1226 are flush with the recess 1230. The configuration shown in FIG. 13 is when the user would be able to slide the upper housing 1216 relative to the base housing 1214 to open the catheter lock system 1202. However, if one protrusion 1248 were pressed slightly further, e.g., to the point when the two flanges 1506, 1252 contact, the second part 1504 of the pin 1248 would slide into the cylindrical recess 1230 reserved for the spring-loaded pins 1226. This would prevent the upper housing 1216 from sliding relative to the base housing 1214. Thus if one or more pins 1248 in the upper housing 1216 are fully depressed by something other than the specific key 1246, those pins 1248 would block the catheter lock system 1202 from opening.

Figure 17:
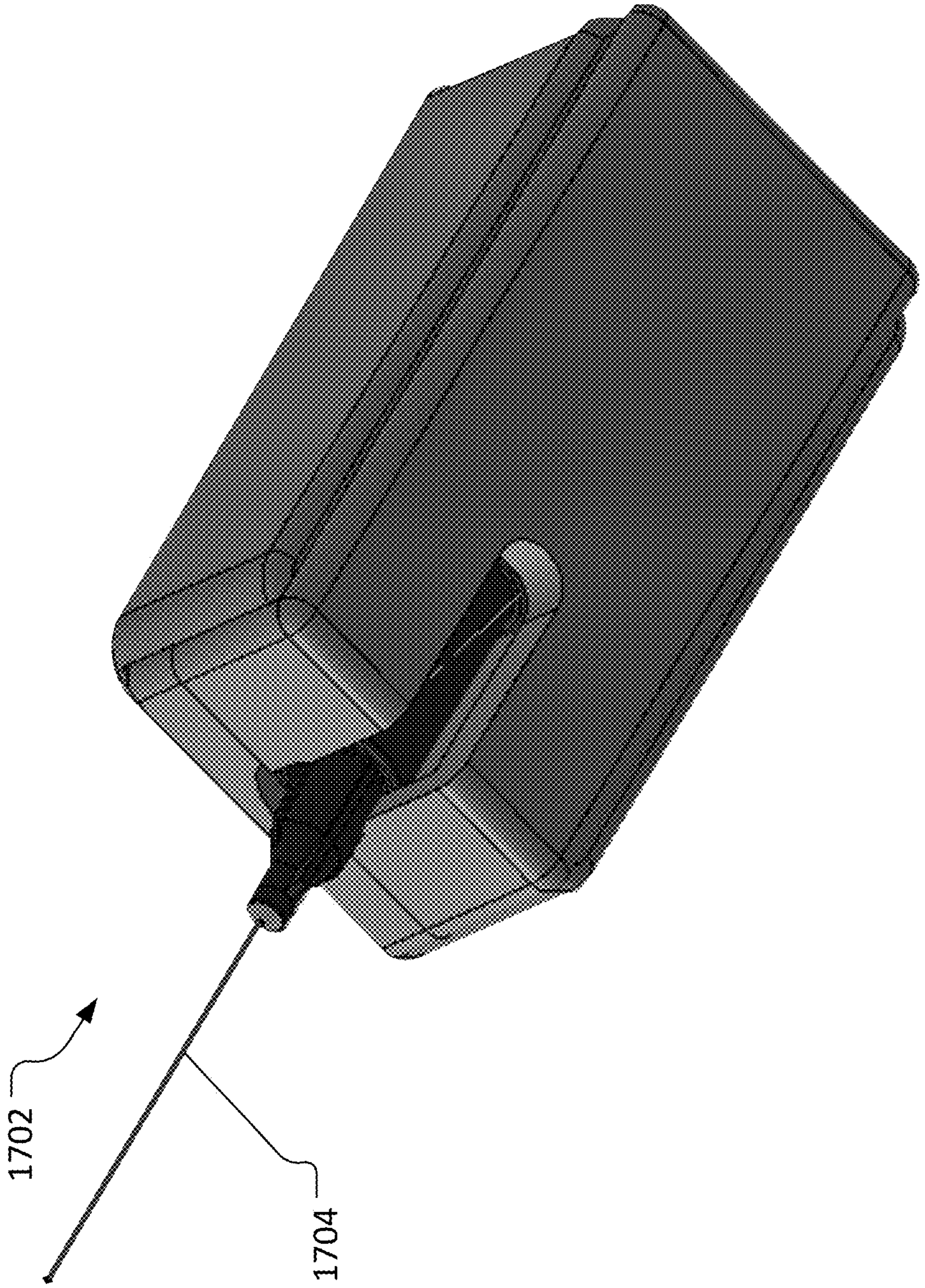
FIG. 17 is a perspective view of a catheter lock system that includes an injection needle.

FIG. 17 shows the catheter lock system 1702 that is substantially similar to the catheter lock system 602 but includes an injection needle 1704 instead of a catheter lines.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of securing access to a catheter hub, the method comprising:

locking the catheter hub in a housing, wherein removal of the catheter hub that is locked in the housing requires unlocking the housing using a key that comprises a plurality of protrusions radially extending from a shank of the key; and fitting the key with a lock mechanism of the housing, wherein the lock mechanism comprises one or more lock disc cams comprising one or more openings, each lock disc cam of the one or more lock disc cams comprising a cam feature.

2. The method of claim 1, further comprising inserting the key into the housing to unlock the housing.

3. The method of claim 1, wherein locking the catheter hub in the housing comprises:

placing the catheter hub in the housing when housing is open; and closing the housing.

4. The method of claim 3, wherein the housing is a clamshell housing comprising a body and a cover that are pivotably connected via a hinge.

5. The method of claim 1, wherein the fitting the lock of the housing with the key prevents other keys that are configured differently than the key from being able to open the locked housing.

6. The method of claim 1, wherein the housing comprises shield inside of the housing and arranged to protect the key from damaging the catheter hub.

7. The method of claim 1, wherein the housing comprises one or more interlocking tabs, each interlocking tab of the one or more interlocking tabs having a hook feature.

8. The method of claim 1, wherein the housing comprises a lock mechanism that includes a cylinder, wherein unlocking the housing comprises rotating the cylinder.

9. A method of securing a catheter hub, the method comprising:

locking the catheter hub in a housing that comprises a lock mechanism, wherein the lock mechanism comprises one or more lock disc cams comprising one or more openings, each lock disc cam of the one or more lock disc cams comprising a cam feature, wherein removal of the catheter hub that is locked in the housing requires unlocking the lock mechanism of the housing.

10. The method of claim 9, wherein the lock mechanism comprises a cylinder, and wherein unlocking the lock mechanism of the housing comprises rotating the cylinder.

11. The method of claim 9, wherein the housing comprises one or more interlocking tabs, each interlocking tab of the one or more interlocking tabs having a hook feature.

12. The method of claim 9, further comprising inserting a key into the housing to unlock the housing, wherein the key comprises a plurality of protrusions radially extending from a shank of the key.

13. The method of claim 9, wherein locking the catheter hub in the housing comprises:

placing the catheter hub in the housing when housing is open; and closing the housing.

14. The method of claim 9, wherein the housing is a clamshell housing comprising a body and a cover that are pivotably connected via a hinge.

15. The method of claim 9, further comprising fitting a key with the lock mechanism of the housing.

16. The method of claim 15, wherein the fitting the lock mechanism of the housing with the key prevents other keys that are configured differently than the key from being able to open the locked housing.

17. The method of claim 15, wherein the housing comprises a shield protruding inside the housing and arranged to protect the key from damaging the catheter hub.

* * * * *